(12) United States Patent
Kim et al.

(10) Patent No.: US 9,580,497 B2
(45) Date of Patent: Feb. 28, 2017

(54) ANTIBODY SPECIFICALLY BINDING TO ANG2 AND USE THEREOF

(71) Applicant: Samsung Electronics Co., Ltd., Suwon-si, Gyeonggi-do (KR)

(72) Inventors: Kyung Eun Kim, Yongin-si (KR); Yoon Sook Lee, Gyeonggi-do (KR); Sang Yeul Han, Yongin-si (KR); Hyung-Chan Kim, Yongin-si (KR); Kwang Hoon Lee, Gyeonggi-do (KR); Hyo Seon Lee, Gyeonggi-do (KR); Seok Kyun Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/606,441

(22) Filed: Jan. 27, 2015

(65) Prior Publication Data

US 2015/0210761 A1 Jul. 30, 2015

(30) Foreign Application Priority Data

Jan. 27, 2014 (KR) .................. 10-2014-0009815

(51) Int. Cl.
| | |
|---|---|
| *A61K 39/395* | (2006.01) |
| *C07K 16/00* | (2006.01) |
| *C07K 16/28* | (2006.01) |
| *C07K 16/22* | (2006.01) |
| *G01N 33/68* | (2006.01) |
| *C07K 16/30* | (2006.01) |
| *A61K 39/00* | (2006.01) |

(52) U.S. Cl.
CPC .......... *C07K 16/22* (2013.01); *C07K 16/3046* (2013.01); *G01N 33/6872* (2013.01); *A61K 2039/505* (2013.01); *C07K 2317/34* (2013.01); *C07K 2317/76* (2013.01); *C07K 2317/92* (2013.01); *G01N 2333/515* (2013.01); *G01N 2500/04* (2013.01)

(58) Field of Classification Search
None
See application file for complete search history.

(56) References Cited

U.S. PATENT DOCUMENTS

| | | | | |
|---|---|---|---|---|
| 5,567,440 | A * | 10/1996 | Hubbell | A61K 9/5031 424/484 |
| 5,859,205 | A * | 1/1999 | Adair | C07K 16/18 530/387.1 |
| 6,455,035 | B1 | 9/2002 | Suri et al. | |
| 7,052,695 | B2 | 5/2006 | Kalish | |
| 2002/0123054 | A1 | 9/2002 | Hillman et al. | |
| 2008/0267971 | A1 | 10/2008 | Green et al. | |
| 2011/0027286 | A1 | 2/2011 | Thurston et al. | |
| 2011/0044998 | A1 | 2/2011 | Bedian et al. | |
| 2011/0150895 | A1 | 6/2011 | Ryu et al. | |
| 2012/0052073 | A1 | 3/2012 | Green et al. | |
| 2012/0141499 | A1 | 6/2012 | Oliner et al. | |
| 2012/0142091 | A1 | 6/2012 | Brinkmann et al. | |
| 2014/0113858 | A1 * | 4/2014 | Han | C07K 14/001 514/7.6 |
| 2014/0302039 | A1 * | 10/2014 | Jeong | C07K 16/22 424/138.1 |

OTHER PUBLICATIONS

Paul, Fundamental Immunology, 3rd Edition, 1993, pp. 292-295.*
Campbell A, General properties and applications of monoclonal antibodies, Elsevier Science Publishers, section 1.1, pp. 1-32, 1984.*
Leow CC, Coffman K, Inigo I, Breen S, Czapiga M, et al. (2012) MEDI3617, a human anti-Angiopoietin 2 monoclonal antibody, inhibits angiogenesis and tumor growth in human tumor xenograft models. Int J Oncol 40: 1321-1330.*
Brown et al. A human monoclonal anti-ANG2 antibody leads to broad antitumor activity in combination with VEGF inhibitors and chemotherapy agents in preclinical models. Mol Cancer Ther. Jan. 2010;9(1):145-56.*
Oliner et al. Suppression of angiogenesis and tumor growth by selective inhibition of angiopoietin-2. Cancer Cell, 2004, 6:507-516.*
Eduardo Padlan, Anatomy of the antibody molecule. Mol Immunol. Feb. 1994;31(3):169-217.*
Rudikoff et al Single amino acid substitution altering antigen-binding specificity. Proc Natl Acad Sci U S A. Mar. 1982;79(6):1979-83.*

* cited by examiner

*Primary Examiner* — Maher Haddad
(74) *Attorney, Agent, or Firm* — Leydig, Voit & Mayer, Ltd.

(57) ABSTRACT

An Ang2 specific antibody, a method of preventing and/or treating a disease related to the activation and/or overproduction (overexpression) of Ang2 by administering the antibody to a subject, and a method of screening a candidate substance for diagnosing, preventing, or treating a disease related to activation or overproduction of Ang2.

4 Claims, 5 Drawing Sheets

ANTIBODY SPECIFICALLY BINDING TO ANG2 AND USE THEREOF

CROSS-REFERENCE TO RELATED APPLICATIONS

This application claims the benefit of Korean Patent Application No. 10-2014-0009815 filed on Jan. 27, 2014 in the Korean Intellectual Property Office, the entire disclosure of which is hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted concurrently herewith and identified as follows: One 25,877 Byte ASCII (Text) file named "719241 ST25.TXT-Revised" created on Jan. 26, 2015.

BACKGROUND OF THE INVENTION

1. Field

Provided is an antibody specifically binding to an angiogenesis-inducing factor angiopoietin-2 (Ang2) to inhibit the function thereof, and a use thereof. In particular, provided are an Ang2 specific antibody, a method of preventing and/or treating a disease related to the activation and/or overproduction (overexpression) of Ang2, including administering the antibody to a subject in need thereof, and a method of screening a candidate substance for diagnosing, preventing, or treating a disease related to activation or overproduction of Ang2.

2. Description of the Related Art

Angiogenesis refers to a mechanism through which a new blood vessel is formed from a pre-existing blood vessel, and has been known to play an essential role in the formation of organs, normal physiological growth, wound healing and so on. Also, abnormal angiogenesis has been known to play a crucial role in diseases or symptoms, such as tumor growth and metastasis, age-related macular degeneration, diabetic retinopathy, psoriasis, rheumatoid arthritis, chronic inflammation, and the like.

Angiogenesis has been known to play an important role in tumor growth and metastasis, and various intensive research into angiogenesis mechanisms for developing new cancer therapies has been going on by developed countries and multinational pharmaceutical companies. One of the proteins that has been a target of such research is Angiopoietin, which has been known to be involved in blood vessel development and angiogenesis after birth. Known are Ang-1, 2, 3 and 4.

Among them, angiogenesis process related to Angiopoietin-2 (Ang2) in a cancer tissue is thought to be as follows. First, for angiogenesis in the cancer tissue, cooption occurs, wherein cancer cells select pre-existing blood vessels to form new blood vessels in a cancer tissue. Thereafter, blood vessel regression occurs, during which the functions of the pre-existing blood vessels are destroyed by Ang2 pathway. The regression of the pre-existing vessels causes hypoxic environment within the cancer tissue, which is an environment where the formation of new blood vessels is possible. Under such conditions, the expression of vascular endothelial cell growth factor (VEGF) is increased, and new blood vessels are thus formed. For such a reason, Ang2 is one of the important targets in the development of angiogenesis inhibitors, and various kinds of angiogenesis inhibitors are currently being developed and actively undergoing preclinical or clinical trials.

As Ang2 is of increasing importance as a target for developing an angiogenesis inhibitor, there is a need of developing an effective and strong Ang2 targeting substance.

BRIEF SUMMARY OF THE INVENTION

One embodiment provides an anti-Ang2 antibody or an antigen-binding fragment thereof, which specifically binds to Ang2.

Another embodiment provides a pharmaceutical composition including the anti-Ang2 antibody or an antigen-binding fragment thereof as an active ingredient.

Another embodiment provides a method of inhibiting angiogenesis, including administering the anti-Ang2 antibody or an antigen-binding fragment thereof to a subject.

Another embodiment provides a method of preventing and/or treating a disease related to activation or overproduction (overexpression) of Ang2, including administering the anti-Ang2 antibody or an antigen-binding fragment thereof to a subject.

Another embodiment provides a method of screening a substance for utility in diagnosing, preventing, or treating a disease related to activation or overproduction of Ang2.

Still another embodiment provides a novel polypeptide comprising an antigen binding site for an anti-Ang2 antibody.

DETAILED DESCRIPTION OF THE INVENTION

Figure 1:
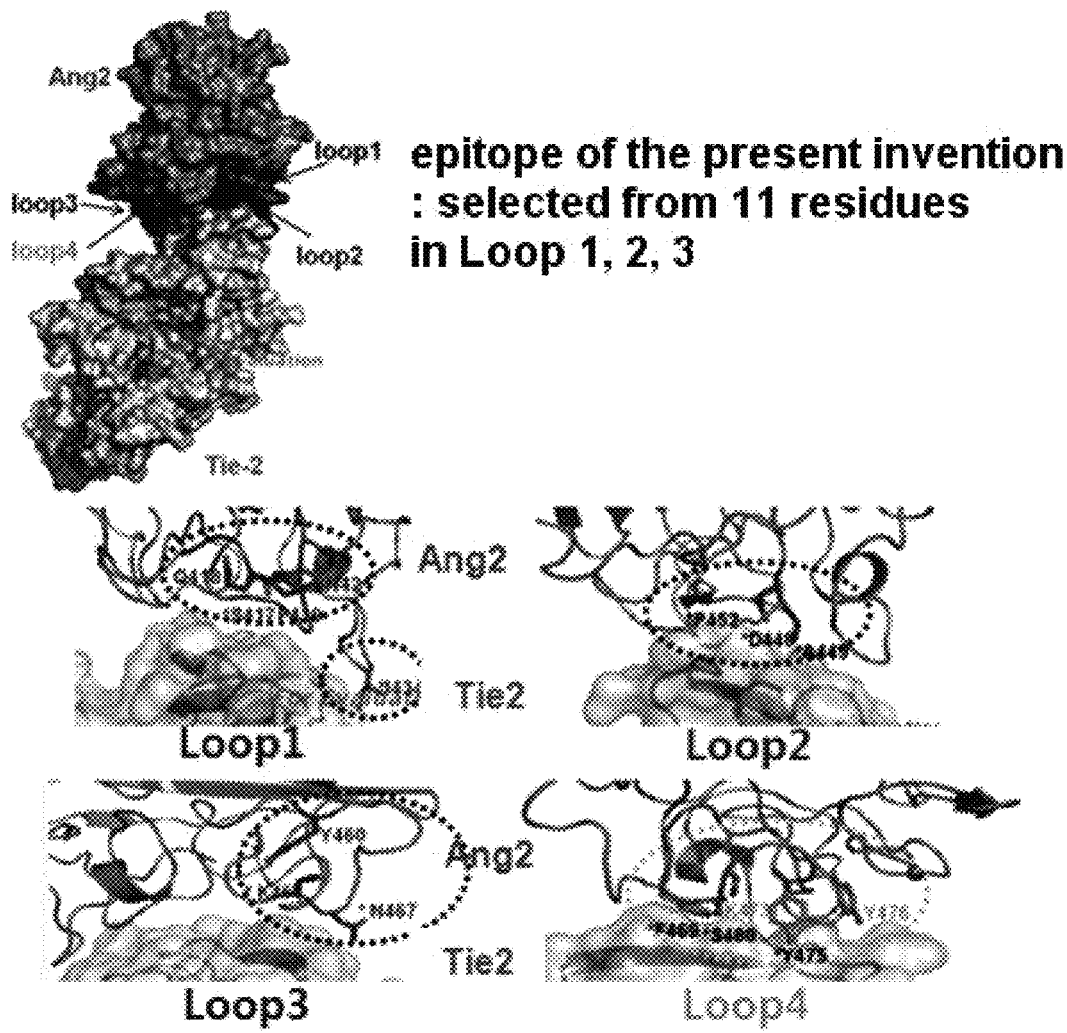
FIG. 1 is a schematic diagram showing an Ang2 antibody binding region (epitope) on Ang2.

Described is an antibody inhibiting the functions of an angiogenesis-inducing factor angiopoietin-2 (Ang2), and particularly, an antibody useful for diagnosing and/or treating a disease associated with the activation and/or overproduction (overexpression) of Ang2 and suppressing angiogenesis in a cancer tissue, by hindering an angiogenesis inducing factor, Ang2, which is essential for the growth of cancer cells in the cancer tissue, from binding to its intracellular receptor, Tie2 receptor.

Ang2 protein is closely related to angiogenesis. It is a soluble ligand present in the blood, and it is a therapeutic target protein which attracts attention for new drug development. Provided is an anti-Ang2 antibody or an antigen-binding fragment thereof, capable of recognizing and binding to Ang2 (e.g., a human Ang2) protein that is widely involved in angiogenesis, metastasis, cancer cell invasion, and the like, thereby preventing Ang2 from binding to its receptor, Tie2 receptor. Therefore, the anti-Ang2 antibody capable of suppressing angiogenesis, cancer incidence, and cancer cell metastasis, and can be used for diagnosis and/or treatment of a disease associated with the activation and/or overproduction (overexpression) of Ang2.

The term "antibody" as used herein refers to a substance generated by the stimulus of an antigen in immune system, and is not particularly limited to specific kinds. The antibody in the invention includes any animal antibodies, chimeric antibodies, humanized antibodies or fully human antibodies. Furthermore, the antibody in the invention also includes antigen-binding fragments of an antibody which possess an antigen binding potential. The term "antibody" is used broadly to encompass antigen-binding antibody fragments unless otherwise noted. Meanwhile, complementarity-determining regions (CDR) as used herein refer to regions which contribute specificity for antigen binding, as part of the variable regions of an antibody. The antigen-binding fragments of an antibody may be antibody fragments including at least one complementarity-determining region.

In connection with angiogenesis process in a cancer tissue, cooption occurs, wherein cancer cells select pre-existing blood vessels to form new blood vessels in a cancer tissue. Thereafter, blood vessel regression occurs, during which the functions of the pre-existing blood vessels are destroyed by Ang2 pathway. The regression of the pre-existing vessels causes hypoxic environment within the cancer tissue, which is an environment where the formation of new blood vessels is possible. Under such conditions, the expression of vascular endothelial cell growth factor (VEGF) is increased, and new blood vessels are thus formed. As angiopoietin proteins, Ang1, Ang2, Ang3, and Ang4, are known and of them, Ang2 is also known as ANGPT2 and is expressed in blood vessel remodeling areas.

Ang2, which becomes a target of an antibody to be provided in one embodiment, is closely related to angiogenesis, is a soluble ligand present in blood, and it is widely involved in angiogenesis, metastasis, and cancer cell invasion. The Ang2 may be derived (originated) from mammals including primates such as humans and monkeys and rodents such as rats and mice and for example, it may be selected from the group consisting of a human Ang2 (e.g., NCBI Accession #O15123), a monkey Ang2 (e.g., NCBI Accession No. Q8MIK6 etc.), a mouse Ang2 (NCBI Accession # NP_031452, Accession #O35608, etc.), a rat Ang2 (e.g., NCBI Accession No. O35462, etc.), and any combination thereof.

Presently, antibodies are widely used for treating diseases. As antibodies are very stable in vivo as well as in vitro and have a long half-life, they are favorable for mass expression and production. Also, since an antibody has intrinsically a dimer structure, it has a fairly high avidity.

In one embodiment, the antibody has an activity of binding to Ang2 and an effect of suppressing angiogenesis in a cancer tissue by hindering Ang2 from binding to its intracellular receptor, Tie2 receptor. Specifically, the antibody may inhibit binding between Ang2 and Tie2 receptor by competing with Tie2 in binding to Ang2 and for example, it may inhibit binding between Ang2 and Tie2 receptor by recognizing and/or binding to a binding site of Ang2 for binding to Tie2 receptor.

An embodiment provides an anti-Ang2 antibody or an antigen-binding fragment thereof. The anti-Ang2 antibody may recognize all or a part (for example, at least one amino acid selected from the group consisting of the amino acid residue regions exposed to the outside of each loop) of the regions consisting of loop 3 (a region covering from 460$^{th}$ to 468$^{th}$ amino acids of SEQ ID NO: 27) of human Ang2 (hAng2; SEQ ID NO: 27; Accession #O15123), or an amino acid sequence region including about 2 to about 20, about 2 to about 15, about 2 to about 10, or about 2 to about 5 consecutive amino acids including at least one exposed amino acid residue, which is exposed to the outside of loop 3 of SEQ ID NO: 27, as an epitope, or specifically bind to the region. An "exposed" amino acid refers to an amino acid that is exposed to solution and available for binding when a protein (e.g., Ang2) is in its native conformation in a biological medium or other solution under physiological conditions (e.g., physiological pH, isotonicity, temperature, etc.).

For example, the amino acid residue exposed to the outside of loop 3 of SEQ ID NO: 27 may be at least one selected from the group consisting of Y460 and K468 (which are marked in bold and italic letters in the following sequence).

Ang2
(SEQ ID NO: 27)
MWQIVFFTLS CDLVLAAAYN NFRKSMDSIG KKQYQVQHGS

CSYTFLLPEM

DNCRSSSSPY VSNAVQRDAP LEYDDSVQRL QVLENIMENN

TQWLMKLENY

IQDNMKKEMV EIQQNAVQNQ TAVMIEIGTN LLNQTAEQTR

KLTDVEAQVL

NQTTRLELQL LEHSLSTNKL EKQILDQTSE INKLQDKNSF

LEKKVLAMED KHIIQLQSIK EEKDQLQVLV SKQNSIIEEL

EKKIVTATVN NSVLQKQQHD LMETVNNLLT MMSTSNSAKD

PTVAKEEQIS FRDCAEVFKS GHTTNGIYTL TFPNSTEEIK

AYCDMEAGGG GWTIIQRRED GSVDFQRTWK EYKVGFGNPS

GEYWLGNEFV SQLTNQQRYV LKIHLKDWEG NEAYSLYEHF

YLSSEELNYR

IHLKGLTGTA GKISSISQPG NDFSTKDGDN DKCICKCSQM

LTGGWWFDAC GPSNLNGMY*Y PQRQNTNK*FN GIKWYYWKGS

GYSLKATTMM IRPADF

For example, the anti-Ang2 antibody may recognize at least one amino acid residue selected from the group consisting of Y460 and K468 positioned at loop 3 of human Ang2 of SEQ ID NO: 27, or an amino acid sequence region including about 2 to about 20, about 2 to about 15, about 2 to about 10, or about 2 to about 5 consecutive amino acids including the above at least one amino acid residue, as an epitope, and/or specifically bind thereto.

The above epitope sites are exposed amino acid residues positioned at loop 3 of the three dimensional structure of Ang2, and they directly participate in binding with a Tie2 receptor or they are positioned within the binding site with the Tie2 receptor or neighboring thereupon (see FIG. 1). Accordingly, the anti-Ang2 antibody or an antigen-binding fragment thereof recognizing and binding to the above at least one epitope competes with the Tie2 receptor to bind to Ang2 and thus, inhibits binding between Ang2 and the Tie2 receptor.

The term "consecutive amino acid" may refer to amino acids which are adjacent to one another on the secondary or tertiary structure of a protein as well as amino acids which are continuous on their primary amino acid sequences. Accordingly, the "consecutive amino acid residues" as used herein may refer to contiguous amino acid residues on the primary, secondary, or tertiary structure of a protein.

In addition, not only an anti-Ang2 antibody recognizing and/or specifically binding to the epitope sites, but also an antibody or an antigen-binding fragment thereof which competes with the anti-Ang2 antibody for binding to Ang2 can compete with the Tie2 receptor to bind to Ang2. Therefore, the antibody (competitively-binding antibody) or an antigen-binding fragment thereof which competes with the anti-Ang2 antibody for binding to Ang2 can inhibit binding between Ang2 and the Tie2 receptor. This competitively-binding antibody may be an antibody recognizing a site adjacent to the aforementioned epitopes on its three dimensional structure as an epitope. The competitively-binding antibody may have an Ang2 binding affinity (Kd) of about 10 nM or less, for example, about 1 pM to about 10 nM, about 10 pM to 10 nM, or about 100 pM to about 10 nM.

Therefore, the anti-Ang2 antibody or an antigen-binding fragment thereof may be at least one selected from the group consisting of an antibody or an antigen-binding fragment thereof recognizing and/or specifically binding to the aforementioned epitope, and an antibody competing therewith for binding to Ang2 or an antigen-binding fragment thereof.

In a particular embodiment, the anti-Ang2 antibody or an antigen-binding fragment thereof may comprise, as a heavy chain complementarity determining region (CDR), at least one selected from the group consisting of a polypeptide (CDR-H1) comprising the amino acid sequence selected from the group consisting of SEQ ID NO: 1, SEQ ID NO: 2, SEQ ID NO: 3, and SEQ ID NO: 4, a polypeptide (CDR-H2) comprising the amino acid sequence selected from the group consisting of SEQ ID NO: 5, SEQ ID NO: 6, SEQ ID NO: 7, and SEQ ID NO: 8, and a polypeptide (CDR-H3) comprising an amino acid sequence selected from the group consisting of SEQ ID NO: 9, SEQ ID NO: 10, SEQ ID NO: 11, and SEQ ID NO: 12.

The anti-Ang2 antibody or an antigen-binding fragment thereof may comprise, as a light chain complementarity determining region (CDR), at least one selected from the group consisting of a polypeptide (CDR-L1) comprising the amino acid sequence of SEQ ID NO: 13, SEQ ID NO: 14, SEQ ID NO: 15, or SEQ ID NO: 16, a polypeptide (CDR-L2) comprising the amino acid sequence of General Formula 1 (SEQ ID NO: 25), and a polypeptide (CDR-L3) comprising an amino acid sequence of General Formula 2 (SEQ ID NO: 26):

[General Formula 1]
(SEQ ID NO: 25)
$X_1-X_2-S-X_3-X_4-X_5-X_6$ wherein $X_1$ is arginine(R) or tyrosine(Y), $X_2$ is alanine(A) or threonine(T) (for example, alanine(A)), $X_3$ is asparagine(N), arginine(R), or serine(S) (for example, asparagine(N)), $X_4$ is leucine(L) or arginine(R), $X_5$ is aspartic acid(D), histidine(H), or tyrosine(Y) (for example, aspartic acid(D), or tyrosine(Y)), and $X_6$ is serine(S) or proline(P);

[General Formula 2]
(SEQ ID NO: 26)
$Q-Q-X_7-X_8-X_9-X_{10}-P-X_{11}-T$ wherein $X_7$ is serine(S), glycine(G), aspartic acid(D), or tyrosine(Y) (for example, serine(S) or aspartic acid(D)), $X_8$ is asparagine(N), tyrosine(Y), or serine(S) (for example, asparagine(N) or tyrosine(Y)), $X_9$ is glutamic acid(E), threonine(T), or lysine(K) (for example, glutamic acid(E) or threonine(T)), $X_{10}$ is aspartic acid(D), serine(S), or leucine(L) (for example, aspartic acid(D) or serine(S)), and $X_{11}$ is leucine(L), tryptophan(W), or tyrosine(Y) (for example, leucine(L) or tryptophan(W)).

In a specific embodiment, the anti-Ang2 antibody or an antigen-binding fragment thereof may comprise or consist essentially of the above heavy chain complementarity determining region, light chain complementarity determining region, or combination thereof.

In particular, the anti-Ang2 antibody or an antigen-binding fragment thereof may comprise or consist essentially of:

at least one heavy chain complementarity determining region selected from the group consisting of a polypeptide (CDR-H1) comprising the amino acid sequence of SEQ ID NO: 1 or SEQ ID NO: 2, a polypeptide (CDR-H2) comprising the amino acid sequence of SEQ ID NO: 5 or SEQ ID NO: 6, and a polypeptide (CDR-H3) comprising an amino acid sequence of SEQ ID NO: 9 or SEQ ID NO: 10, or a heavy chain variable region comprising the at least one heavy chain complementarity determining region;

at least one light chain complementarity determining region selected from the group consisting of a polypeptide (CDR-L1) comprising the amino acid sequence of SEQ ID NO: 13 or SEQ ID NO: 14, a polypeptide (CDR-L2) comprising the amino acid sequence of SEQ ID NO: 25, and a polypeptide (CDR-L3) comprising the amino acid sequence of SEQ ID NO: 26, or a light chain variable region comprising the at least one light chain complementarity determining region;

a combination of the at least one heavy chain complementarity determining region and the at least one light chain complementarity determining region; or a combination of the heavy chain variable region and the light chain variable region.

More particularly, the anti-Ang2 antibody or an antigen-binding fragment thereof may comprise or consist essentially of:

at least one heavy chain complementarity determining region selected from the group consisting of a polypeptide (CDR-H1) comprising the amino acid sequence of SEQ ID NO: 1 or SEQ ID NO: 2, a polypeptide (CDR-H2) comprising the amino acid sequence of SEQ ID NO: 5 or SEQ ID NO: 6, and a polypeptide (CDR-H3) comprising an amino acid sequence of SEQ ID NO: 9 or SEQ ID NO: 10, or a heavy chain variable region comprising the at least one heavy chain complementarity determining region;

at least one light chain complementarity determining region selected from the group consisting of a polypeptide (CDR-L1) comprising the amino acid sequence of SEQ ID NO: 13 or SEQ ID NO: 14, a polypeptide (CDR-L2) comprising the amino acid sequence of SEQ ID NO: 17 or SEQ ID NO: 18, and a polypeptide (CDR-L3) comprising the amino acid sequence of SEQ ID NO: 21 or SEQ ID NO: 22, or a light chain variable region comprising the at least one light chain complementarity determining region;

a combination of the at least one heavy chain complementarity determining region and the at least one light chain complementarity determining region; or a combination of the heavy chain variable region and the light chain variable region.

In one embodiment, the heavy chain variable region may comprise or consist essentially of the amino acid sequence of SEQ ID NO: 28 or SEQ ID NO: 29, and the light chain variable region may comprise or consist essentially of the amino acid sequence of SEQ ID NO: 36 or SEQ ID NO: 37.

The anti-Ang2 antibody or an antigen-binding fragment thereof may not be one consisting of at least one selected from the group consisting of SEQ ID NO: 14, SEQ ID NO: 18, and SEQ ID NO: 22, or may not be one consisting of the amino acid sequence of SEQ ID NO: 37 only.

In another embodiment, the anti-Ang2 antibody or an antigen-binding fragment thereof may comprise or consist essentially of:

at least one heavy chain complementarity determining region selected from the group consisting of a polypeptide (CDR-H1) comprising the amino acid sequence of SEQ ID NO: 3, a polypeptide (CDR-H2) comprising the amino acid sequence of SEQ ID NO: 7, and a polypeptide (CDR-H3) comprising an amino acid sequence of SEQ ID NO: 11, or a heavy chain variable region comprising the at least one heavy chain complementarity determining region;

at least one light chain complementarity determining region selected from the group consisting of a polypeptide (CDR-L1) comprising the amino acid sequence of SEQ ID NO: 15, a polypeptide (CDR-L2) comprising the amino acid sequence of SEQ ID NO: 19, and a polypeptide (CDR-L3) comprising the amino acid sequence of SEQ ID NO: 23, or a light chain variable region comprising the at least one light chain complementarity determining region;

a combination of the at least one heavy chain complementarity determining region and the at least one light chain complementarity determining region; or a combination of the heavy chain variable region and the light chain variable region.

In one embodiment, the heavy chain variable region may comprise or consist essentially of the amino acid sequence of SEQ ID NO: 30, and the light chain variable region may comprise or consist essentially of the amino acid sequence of SEQ ID NO: 38.

In another embodiment, the anti-Ang2 antibody or an antigen-binding fragment thereof may comprise or consist essentially of:

at least one heavy chain complementarity determining region selected from the group consisting of a polypeptide (CDR-H1) comprising the amino acid sequence of SEQ ID NO: 4, a polypeptide (CDR-H2) comprising the amino acid sequence of SEQ ID NO: 8, and a polypeptide (CDR-H3) comprising an amino acid sequence of SEQ ID NO: 12, or a heavy chain variable region comprising the at least one heavy chain complementarity determining region;

at least one light chain complementarity determining region selected from the group consisting of a polypeptide (CDR-L1) comprising the amino acid sequence of SEQ ID NO: 16, a polypeptide (CDR-L2) comprising the amino acid sequence of SEQ ID NO: 20, and a polypeptide (CDR-L3) comprising the amino acid sequence of SEQ ID NO: 24, or a light chain variable region comprising the at least one light chain complementarity determining region;

a combination of the at least one heavy chain complementarity determining region and the at least one light chain complementarity determining region; or a combination of the heavy chain variable region and the light chain variable region.

In one embodiment, the heavy chain variable region may comprise or consist essentially of the amino acid sequence of SEQ ID NO: 31, and the light chain variable region may comprise or consist essentially of the amino acid sequence of SEQ ID NO: 39.

The heavy chain CDR of the anti-Ang2 antibody may comprise amino acid sequences, for example, as set forth in the following Table 1.

TABLE 1

| Amino acid sequence of heavy chain CDR | | |
| --- | --- | --- |
| CDRH1-KABAT | CDRH2-KABAT | CDRH3-KABAT |
| SYWLE (SEQ ID NO: 1) | EILPGSGSTNYNEKFRG (SEQ ID NO: 5) | GNHNSYYYAMDY (SEQ ID NO: 9) |
| DYYMK (SEQ ID NO: 2) | EINPKNGDTFYNQIFKG (SEQ ID NO: 6) | ENDYDVGFFDY (SEQ ID NO: 10) |
| NYGMN (SEQ ID NO: 3) | WINTYTGEPTYADDFKG (SEQ ID NO: 7) | DHDGYLMDY (SEQ ID NO: 11) |
| DPYIH (SEQ ID NO: 4) | RIDPANGNTKYDPKFQG (SEQ ID NO: 8) | RWDGGGFDY (SEQ ID NO: 12) |

The light chain CDR of the anti-Ang2 antibody may comprise amino acid sequences, for example, as set forth in the following Table 2.

TABLE 2

| Amino acid sequence of light chain CDR | | |
| --- | --- | --- |
| CDRL1-KABAT | CDRL2-KABAT | CDRL3-KABAT |
| RASESVDSYGNSFMH (SEQ ID NO: 13) | RASNLDS (SEQ ID NO: 17) | QQSNEDPLT (SEQ ID NO: 21) |
| KASQSVSNDVA (SEQ ID NO: 14) | YASNRYP (SEQ ID NO: 18) | QQDYTSPWT (SEQ ID NO: 22) |
| STSQGISNYLN (SEQ ID NO: 15) | YTSSLHS (SEQ ID NO: 19) | QQYSKLPYT (SEQ ID NO: 23) |
| RASQDISNYLN (SEQ ID NO: 16) | YTSRLHS (SEQ ID NO: 20) | QQGNTLPWT (SEQ ID NO: 24) |

An animal-derived antibody which is produced by immunizing an animal with a desired antigen may generally trigger an immune rejection response when administered to humans for treatment purpose, and a chimeric antibody has been developed to suppress such immune rejection response. A chimeric antibody is formed by replacing the constant region of an animal-derived antibody, which is a cause of anti-isotype response, with the constant region of a human antibody using genetic engineering methods. The chimeric antibody has considerably improved anti-isotype response in comparison with animal-derived antibodies, but animal-derived amino acids are still present in its variable regions and thus it still contains potential side effects resulting from an anti-idiotypic response. It is a humanized antibody that has been thus developed to improve such side effects. This is manufactured by grafting CDR (complementarity determining regions) which, of the variable regions of a chimeric antibody, has an important role in antigen binding into a human antibody framework.

An important consideration in CDR grafting technology for manufacturing a humanized antibody is to select an optimized human antibody which can optimally incorporate the CDR of an animal-derived antibody and for this, utilization of antibody database, analysis of crystal structure, molecule modeling technology, etc. are employed. However, although the CDR of an animal-derived antibody is grafted into an optimized human antibody framework, there are a considerable number of cases where antigen binding affinity is not preserved because there are amino acids which affect antigen binding while being positioned at the framework of the animal-derived antibody. In this regard, it may be essential to apply an additional antibody engineering technology for restoring antigen binding affinity.

According to one embodiment, the antibody may be a mouse-derived antibody, a mouse-human chimeric antibody, a humanized antibody, or a human antibody. The antibody or antigen-binding fragment thereof may be isolated from a living body or non-naturally occurring. The antibody or antigen-binding fragment thereof may be recombinant or synthetic. The antibody or antigen-binding fragment thereof may be monoclonal.

An intact antibody has a structure with two full-length light chains and two full-length heavy chains, and each light chain is linked to each heavy chain via a disulfide bond. The constant region of an antibody is divided into a heavy chain constant region and a light chain constant region, and the heavy chain constant region has gamma ($\gamma$), mu ($\mu$), alpha ($\alpha$), delta ($\delta$) and epsilon ($\epsilon$) types, and has gamma1 ($\gamma$1), gamma2 ($\gamma$2), gamma3 ($\gamma$3), gamma4 ($\gamma$4), alpha1 ($\alpha$1) and alpha2 ($\alpha$2) as its subclass. The light chain constant region has kappa ($\kappa$) and lambda ($\lambda$) types.

The term "heavy chain" is understood to include a full-length heavy chain and fragments thereof, the full-length heavy chain including a variable region domain $V_H$ including an amino acid sequence having sufficient variable region sequences that contribute the specificity for antigen binding and three constant region domains $C_{H1}$, $C_{H2}$ and $C_{H3}$ domains and a hinge. The term "light chain" is understood to include a full-length light chain and fragments thereof, the full-length light chain including a variable region domain $V_L$ including an amino acid sequence having sufficient variable region sequences that contribute to the specificity for antigen binding and a constant region domain $C_L$.

The term "CDR (complementarity determining region)" refers to an amino acid sequence found in the hypervariable region of a heavy chain and a light chain of an immunoglobulin. The heavy and light chain may each include three CDRs (CDRH1, CDRH2, CDRH3, and CDRL1, CDRL2, CDRL3). The CDRs of an antibody can provide an essential contact residue for binding to an antigen or an epitope. Throughout the specification, the terms "specifically binding" or "specifically recognizing" has the same meaning as generally known to an ordinary person in the art, indicating that an antigen and an antibody specifically interact with each other to lead to an immunological response.

The light chain constant region and the heavy chain constant region except the aforementioned CDR regions or light chain variable regions and heavy chain variable regions of the anti-Ang2 antibody may be light chain constant regions and heavy chain constant regions of any subtypes of an immunoglobulin, for example, light chain constant regions and heavy chain constant regions of IgA, IgD, IgE, IgG (e.g., IgG1, IgG2, IgG 3, and IgG4), IgM, etc.

In an embodiment, the antigen-binding fragment may at least one be selected from the group consisting of an scFv, an (scFv)$_2$, an scFv-Fc, an Fab, an Fab' and an F(ab')$_2$.

The term "antigen-binding fragment," which is a fragment of the full structure of an immunoglobulin, refers to some of a polypeptide including a portion to which an antigen can bind. For example, it may be an scFv, an (scFv)$_2$, an Fab, an Fab', or an F(ab')$_2$, but is not limited thereto. Among the antigen-binding fragments, an Fab, which is a structure having the light chain and heavy chain variable regions, the light chain constant region, and the heavy chain first constant region ($C_{H1}$), has one antigen binding site.

An Fab' differs from the Fab in that the Fab' has a hinge region including at least one cysteine residue at the C-terminal of the heavy chain $C_{H1}$ domain.

An F(ab')$_2$ antibody is produced when cysteine residues at the hinge region of the Fab' are joined by a disulfide bond. An Fv is a minimal antibody fragment, having only heavy chain variable regions and light chain variable regions, and a recombinant technique for producing the Fv fragment is well known in the art.

A two-chain Fv may have a structure in which heavy chain variable regions are linked to light chain variable regions by a non-covalent bond, and a single-chain Fv may generally form a dimer structure as in the two-chain Fv, wherein heavy chain variable regions are covalently bound to light chain variable regions via a peptide linker or the heavy and light chain variable regions are directly linked to each other at the C-terminals thereof. The peptide linker may include 1 to 100 or 2 to 50 amino acids, and proper sequences thereof have been known in the art.

The antigen-binding fragment may be obtained using a protease (for example, a whole antibody can be digested with papain to obtain Fab fragments, or can be digested with pepsin to obtain F(ab')$_2$ fragments), or may be prepared by a genetic recombinant technique.

The term "hinge region" refers to a region included in the heavy chains of an antibody, which is present between the CH1 and CH2 regions, and provides flexibility to the antigen binding site in the antibody.

When an animal-derived antibody goes through a chimerization process, an animal-derived IgG1 hinge is replaced with a human IgG1 hinge, but a length of the animal-derived IgG1 hinge is shorter than the human IgG1 hinge, and disulfide bonds between two heavy chains are reduced from 3 to 2. Thus, rigidity of the hinges may have different effects. Therefore, modification of a hinge region can increase an antigen binding efficiency of a humanized antibody. Methods of deleting, inserting, or substituting an amino acid for modifying amino acid sequences of the hinge region are well known in the art.

The anti-Ang2 antibody may be a monoclonal antibody. The monoclonal antibody may be prepared by methods well known in the art. For example, it may be prepared using a phage display technique. Alternatively, the anti-Ang2 antibody may also be prepared as a mouse-derived monoclonal antibody using the method of Schwaber, et al. (Schwaber, J and Cohen, E. P., "Human×Mouse Somatic Cell Hybrid Clones Secreting Immunoglobulins of Both Parental Types," Nature, 244 (1973), 444-447).

Meanwhile, individual monoclonal antibodies may be screened using a typical ELISA (Enzyme-Linked ImmunoSorbent Assay) format, based on the binding potential with Ang2 Inhibitory activities can be verified through functional analysis such as competitive ELISA for verifying the molecular interaction of binding assemblies or functional analysis such as a cell-based assay. Then, with regard to monoclonal antibody members selected on the basis of their strong inhibitory activities, their affinities (Kd values) to Ang2 may each be verified.

Finally selected antibodies may be subjected to humanization as well as prepared as an antibody where the portions not including the antigen-binding regions are derived from a human immunoglobulin antibody. The method of humanization is generally known to the relevant art (Almagro, J. C. and Fransson, J., "Humanization of antibodies," Frontiers in Bioscience, 13(2008), 1619-1633).

Another embodiment provides a hybridoma which produces the antibody. The hybridoma may be at least one selected from the group consisting of deposit numbers KCLRF-BP-00305, KCLRF-BP-00306, KCLRF-BP-00307, and KCLRF-BP-00308.

Another embodiment provides a pharmaceutical composition comprising the anti-Ang2 antibody or an antigen-binding fragment thereof. In one embodiment, the pharmaceutical composition may be used for inhibiting angiogenesis. In another embodiment, the pharmaceutical composition may be used for preventing and/or treating a disease associated with activation and/or overexpression of Ang2.

Another embodiment provides a method of inhibiting angiogenesis comprising administering the anti-Ang2 antibody or an antigen-binding fragment thereof to a subject in need of inhibiting angiogenesis. The method of inhibiting angiogenesis may further comprise a step of identifying the subject who is in need of angiogenesis inhibition, before the step of administering. Another embodiment provides a method of preventing and/or treating a disease associated with Ang2 activation and/or overexpression, comprising administering the anti-Ang2 antibody or an antigen-binding fragment thereof to a subject in need of preventing and/or treating the disease. The method of preventing and/or treating a disease associated with Ang2 activation and/or overexpression may further comprise a step of identifying the subject who is in need of preventing and/or treating a disease associated with Ang2 activation and/or overexpression, before the step of administering. In the above methods, the anti-Ang2 antibody or an antigen-binding fragment thereof may be administered in a pharmaceutically effective amount.

The pharmaceutical composition may further include a pharmaceutically acceptable carrier, and the carrier may be those commonly used in the formulation of drugs, which may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but is not limited thereto. The pharmaceutical composition may further include one or more selected from the group consisting of a diluent, an excipient, a lubricant, a wetting agent, a sweetener, a flavor enhancer, an emulsifying agent, a suspension agent, and a preservative.

The pharmaceutical composition may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration leads to digestion of proteins or peptides, an active ingredient in the compositions for oral administration must be coated or formulated to prevent digestion in stomach. In addition, the composition may be administered using an optional device that enables an active substance to be delivered to target cells.

The content of the anti-Ang2 antibody or an antigen-binding fragment thereof in the pharmaceutical composition may be prescribed in a variety of ways, depending on factors such as formulation methods, administration methods, age of subjects, body weight, gender, pathologic conditions, diets, administration time, administration interval, administration route, excretion speed, and reaction sensitivity. For example, a daily dosage of the anti-Ang2 antibody or an antigen-binding fragment thereof may be within the range of 0.001 to 1000 mg/kg, 0.01 to 100 mg/kg, 0.1 to 50 mg/kg, or 0.1 to 20 mg/kg, but is not limited thereto. The daily dosage may be formulated into a single formulation in a unit dosage form or formulated in suitably divided dosage forms, or it may be manufactured to be contained in a multiple dosage container. The term "pharmaceutically effective amount" as used herein refers to a content or dose of an active ingredient capable of showing desirable pharmacological effects and it may be determined in a variety of ways, depending on factors such as formulation methods, administration methods, age of subjects, body weight, gender, pathologic conditions, diets, administration time, administration interval, administration route, excretion speed, and reaction sensitivity.

The pharmaceutical composition may be formulated into a form of a solution in oil or an aqueous medium, a suspension, syrup, an emulsifying solution, an extract, powder, granules, a tablet, or a capsule, and may further include a dispersing or a stabilizing agent for the formulation.

In particular, the pharmaceutical composition comprising the anti-Ang2 antibody or an antigen-binding fragment thereof may be formulated into an immunoliposome since it contains an antibody or an antigen-binding fragment. A liposome containing an antibody may be prepared using any methods widely known in the art. The immunoliposome may be a lipid composition including phosphatidylcholine, cholesterol, and polyethyleneglycol-derivatized phosphatidylethanolamine, and may be prepared by a reverse phase evaporation method. For example, Fab' fragments of an antibody may be conjugated to the liposome through a disulfide-exchange reaction.

Meanwhile, as the anti-Ang2 antibody or an antigen-binding fragment thereof specifically binds to Ang2, this can be used for detecting Ang2, or the activation and/or overproduction (overexpression) of Ang2.

Accordingly, another embodiment provides a composition for detecting Ang2, wherein the composition comprises the anti-Ang2 antibody or the antigen-binding fragment thereof. Another embodiment provides a method for detecting Ang2 comprising contacting the anti-Ang2 antibody or the antigen-binding fragment thereof with a biological sample; and measuring an antigen-antibody reaction. In this detection method, when the antigen-antibody reaction is detected, it can be determined that Ang2 is present in the biological sample. Another embodiment provides a use of the anti-Ang2 antibody or an antigen-binding fragment thereof for detecting Ang2.

Another embodiment provides a composition for detecting the activation and/or overproduction (overexpression) of Ang2, or a pharmaceutical composition for diagnosing a disease related to the activation and/or overproduction (overexpression) of Ang2, wherein the composition comprises the anti-Ang2 antibody or the antigen-binding fragment thereof. Another embodiment provides a method for detecting the activation and/or overproduction (overexpression) of Ang2, or a method for diagnosing a disease related to the activation and/or overproduction (overexpression) of Ang2, or a method of providing information for diagnosis thereof, wherein the method comprises contacting the anti-Ang2 antibody or the antigen-binding fragment thereof with a biological sample obtained from a subject; and measuring an antigen-antibody reaction. The detection method, the diagnose method, or the method of providing information for diagnosis may further comprise a step of determining the subject to have Ang2 activation and/or overproduction (overexpression) symptoms or to have a disease related to Ang2 activation and/or overproduction (overexpression) in case that the antigen-antibody reaction is detected, subsequently to the step of measuring an antigen-antibody reaction. The biological sample may be at least one selected from the group consisting of cells, tissues, and body fluid (e.g., blood, serum, blood plasma, etc.), which are obtained (isolated) from a subject, and culture thereof.

The step of measuring the antigen-antibody reaction may be performed using various methods known in the art. For example, it may be measured through an ordinary enzyme reaction, fluorescence, luminescence, and/or radioactivity detection and particularly, it may be measured by a method selected from the group consisting of immunochromatography, immunohistochemistry, enzyme linked immunosorbent assay (ELISA), radioimmunoassay (RIA), enzyme immunoassay (EIA), fluorescence immunoassay (FIA), luminescence immunoassay (LIA), western blotting, microarray, etc., but is not limited thereto.

The subjects which the anti-Ang2 antibody or an antigen binding fragment is administered to or is aimed to diagnose may be selected from mammals including primates such as humans and monkeys, or rodents such as rats and mice.

The diseases related to the activation and/or overproduction (overexpression) of Ang2 may be cancer; cancer metastasis; cancer invasion/penetration; eye diseases such as retinopathy of prematurity, macular degeneration (e.g., age-related macular degeneration), diabetic retinopathy, neovascular glaucoma, etc.; asthma; rheumatoid arthritis; inflammatory diseases such as psoriasis, chronic inflammation, pneumonia, septicemia, etc.; cardiovascular disease such as hypertension, arteriosclerosis, etc.; sepsis, etc. The cancer may be associated with overexpression of Ang2, it may be a solid cancer or a blood cancer, and it may be, but is not limited to, selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatocellular cancer, gastric cancer, pancreatic cancer, glioblastoma, cervical cancer, ovarian cancer, liver cancer, bladder cancer, hepatoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, osteosarcoma, and the like. The cancer may be a primary cancer or metastatic cancer.

In another embodiment, provided is a method for screening a candidate substance (compound) for utility in diagnosing, preventing, and/or treating a disease related to the activation and/or overproduction (overexpression) of Ang2 using the above epitope. The screening method includes (a) contacting a candidate compound to the aforementioned epitope of three dimensional structure of Ang2; and (b) measuring binding between the epitope and the candidate compound.

In the step of measuring binding, when the epitope and the candidate compound show binding affinity of 10 nM or less, for example, 1 pM to 10 nM, 10 pM to 10 nM, or 100 pM to 10 nM, the candidate compound can be determined to be a candidate substance for diagnosing, preventing, and/or treating a disease related to the activation and/or overproduction (overexpression) of Ang2.

The step of measuring binding may be carried out using various methods known in the art. For example, it may be measured through an ordinary enzyme reaction, fluorescence, luminescence, and/or radioactivity detection and particularly, it may be measured by a method selected from the group consisting of surface plasmon resonance (SPR), immunochromatography, immunohistochemistry, enzyme linked immunosorbent assay (ELISA), radioimmunoassay (RIA), enzyme immunoassay (EIA), fluorescence immunoassay (FIA), luminescence immunoassay (LIA), western blotting, microarray, etc., but is not limited thereto.

The epitope may be all or a part (for example, at least one selected from the group consisting of the amino acid residue regions exposed to the outside of loop 3) of loop 3 (a region covering from $460^{th}$ to $468^{th}$ amino acids of SEQ ID NO: 27) of human Ang2 (hAng2; SEQ ID NO: 27), or an amino acid sequence region including 2 to 20, 2 to 15, 2 to 10, or 2 to 5 contiguous amino acids including at least one amino acid residue exposed to the outside of loop 3 of SEQ ID NO: 27 and for example, it may be at least one amino acid residue selected from the group consisting of Y460 and K468, which are positioned at loop 3, or an amino acid sequence region including 2 to 20, 2 to 15, 2 to 10, or 2 to 5 contiguous amino acids within Ang2, which comprises the above at least one amino acid residue (e.g., Y460 and/or K468).

The candidate compounds may be one or more selected from the group consisting of various artificially-synthesized or natural compounds (chemical), polypeptides, oligopeptides, polynucleotides, oligonucleotides, antisense-RNA, shRNA (short hairpin RNA), siRNA (small interference RNA), aptamers, natural product extracts and so on.

The step of measuring the binding affinity between the epitope and the candidate compound may be carried out using various methods known in the art. For example, the binding affinity may be measured using Biacore machine. In general, the range within which the binding affinity is considered as a drug for treatment may be defined to have a binding constant KD value of 10 mM or less. For instance, in case that the binding affinity between the epitope of Ang2 and a candidate compound (for example, antibody) to be analyzed is 1 pM to 10 nM, 10 pM to 10 nM, or 100 pM to 10 nM when measured using surface plasmon resonance methods such as Biacore machine, the candidate compound (for example, antibody) can be determined to be a candidate substance for diagnosing, preventing, and/or treating a disease related to the activation and/or overproduction (overexpression) of Ang2.

In another embodiment, provided is polypeptide molecule comprising the heavy chain complementarity determining region, the light chain complementarity determining region or the combination thereof or the heavy chain variable region, the light chain variable region or the combination thereof, of the anti-Ang2 antibody as described above. The polypeptide molecule may function as a precursor or a component of an antagonist against Ang2 as well as an antibody or an antigen-binding fragment thereof. For example, the polypeptide molecule may function as an Ang2 antigen binding site, and can be included as a component of a protein scaffold (e.g., peptibody, nanobody, etc.), a bispecific antibody, and a multi-specific antibody having a similar structure to an antibody. The polypeptide molecule may be non-naturally occurring. For example, the polypeptide molecule may be synthetic or recombinant.

The term "antagonist" as used herein is interpreted to encompass all molecules that partially or entirely block, suppress or neutralize at least one biological activity of its target (e.g., Ang2).

The term "peptibody (peptide+antibody)" used herein refers to a fusion protein including a peptide and all or part of the constant region of an antibody such as an Fc portion wherein the peptide serves as an antigen binding site (heavy chain and/or light chain CDR or variable regions) thereby to render a protein having similar framework and functions to an antibody The term "nanobody" used herein is called a single-domain antibody, refers to an antibody fragment including a single variable domain of an antibody as a monomer form, and has characteristics of selectively binding to a specific antigen similarly to an antibody having an intact structure. The molecular weight of the nanobody is generally about 12 kDa to about 15 kDa, which is very little when compared to the normal molecular weight (about 150 kDa or about 160 kDa) of an intact antibody (including two heavy chains and two light chains) and in some cases it is smaller than an Fab fragment or scFv fragment.

The term "bispecific antibody" or "multi-specific antibody" used herein refers to an antibody recognizing and/or binding to two (bispecific antibody) or more (multi-specific antibody) different antigens, or recognizing and/or binding to different sites of the same antigen, and one antigen binding site of the bispecific antibody or multi-specific antibody may include the polypeptide described above.

The polypeptide molecule may comprise or consist essentially of at least one of SEQ ID NOs: 1-24.

In an embodiment, the polypeptide molecule may comprise or consist essentially of:

at least one selected from the group consisting of a polypeptide comprising the amino acid sequence selected from the group consisting of SEQ ID NO: 1, SEQ ID NO: 2, SEQ ID NO: 3, and SEQ ID NO: 4, a polypeptide comprising the amino acid sequence selected from the group consisting of SEQ ID NO: 5, SEQ ID NO: 6, SEQ ID NO: 7, and SEQ ID NO: 8, and a polypeptide comprising an amino acid sequence selected from the group consisting of SEQ ID NO: 9, SEQ ID NO: 10, SEQ ID NO: 11, and SEQ ID NO: 12;

at least one selected from the group consisting of a polypeptide comprising the amino acid sequence of SEQ ID NO: 13, SEQ ID NO: 14, SEQ ID NO: 15, or SEQ ID NO: 16, a polypeptide comprising the amino acid sequence of SEQ ID NO: 25 (for example, an amino acid sequence selected from the group consisting of SEQ ID NOS: 17 to 20), and a polypeptide comprising the amino acid sequence of SEQ ID NO: 26 (for example, an amino acid sequence selected from the group consisting of SEQ ID NOS: 21 to 24); or any combination thereof.

In an embodiment, the polypeptide molecule may comprise or consist essentially of at least one selected from SEQ ID NOS: 28 to 31 and 36 to 39. Specifically, the polypeptide molecule may comprise or consist essentially of the amino acid sequence selected from the group consisting of SEQ ID NOS: 28 to 31; the amino acid sequence selected from the group consisting of SEQ ID NOS: 36 to 39; or any combination thereof.

In an embodiment, the polypeptide molecule may not be one consisting only of at least one selected from the group consisting of amino acid sequences of SEQ ID NO: SEQ ID NO: 14, SEQ ID NO: 18, and SEQ ID NO: 22, or may not be one consisting only of the amino acid sequence of SEQ ID NO: 37.

The above polypeptide molecule may be non-naturally occurring, and for example, may be synthetic or recombinant.

The above bispecific antibody or multi-specific antibody may refer to an antibody including each antigen binding site to different two or more kinds of antigens and recognizing the two or more kinds of antigens at the same time, wherein one of the antigen binding sites may include the aforementioned polypeptide molecule. In particular, the polypeptide molecule serving as Ang2 antigen binding site may form a dimer or multimer together with an antigen binding site to another antigen to constitute a bi-specific antibody or a multi-specific antibody. Accordingly, in one embodiment, there is provided a bi-specific antibody or a multi-specific antibody including the polypeptide molecule as an Ang2 antigen binding site.

In another embodiment, provided is a protein scaffold comprising at least one (e.g., 1 to 5, particularly 2 to 4) peptide complex, which comprises one or more of the aforementioned polypeptide molecules or a repeat where the polypeptide molecules are repeatedly linked by a linker (hereafter, 'first peptide') and a polypeptide having a structural function (hereafter, 'second peptide'; e.g., a heavy chain or light chain constant region of an antibody, or an Fc fragment of an antibody), wherein the at least one peptide complex is bound to each other at the second peptide (e.g., Fc fragment) to form a multimer structure.

In another embodiment, provided is a polynucleotide molecule encoding the polypeptide molecule or a recombinant vector comprising the polynucleotide molecule. Particularly, the polynucleotide molecule may comprise or consist essentially of a nucleotide sequence encoding the amino acid sequence selected from the group consisting of SEQ ID NOS: 28 to 31, or a nucleotide sequence encoding the amino acid sequence selected from the group consisting of SEQ ID NOS: 36 to 39. For example, the polynucleotide molecule may comprise or consist essentially of the nucleotide sequence selected from the group consisting of SEQ ID NOS: 32 to 35, or the nucleotide sequence selected from the group consisting of SEQ ID NOS: 40 to 43.

The term "vector" used herein refers to a means for expressing a target gene in a host cell. For example, the vector may include a plasmid vector, a cosmid vector, and a virus vector, such as a bacteriophage vector, an adenovirus vector, a retrovirus vector, and an adeno-associated virus vector. The recombinant vector may be prepared by manipulating a plasmid (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, and pUC19), a phage (for example, λgt4λB, λ-Charon, λΔz1, and M13), or a virus (for example, SV40) often used in the art, but is not limited thereto.

In the recombinant vector, the polynucleotide may be operatively linked to a promoter. The term "operatively linked" used herein means a functional linkage between a nucleotide expression regulating sequence (for example, a promoter sequence) and other nucleotide sequences. Thus, the regulating sequence may regulate the transcription and/or translation of the other nucleotide sequences by being "operatively linked".

The recombinant vector may be generally constructed as a cloning vector or an expression vector. The expression vector may be a vector commonly used in the art for expressing a foreign protein in a plant, animal or microorganism. The recombinant vector may be constructed using various methods known in the art.

The recombinant vector may be constructed for use in prokaryotic or eukaryotic host cells. For example, when a prokaryotic cell is used as a host cell, the expression vector used generally includes a strong promoter capable of initiating transcription (for example, pL$^\lambda$ promoter, CMV promoter, trp promoter, lac promoter, tac promoter, T7 promoter), a ribosome binding site for initiating translation, and a transcription/translation termination sequence. When a eukaryotic cell is used as a host cell, an origin of replication acting in the eukaryotic cell to be included in the vector may include fl origin of replication, SV40 origin of replication, pMB1 origin of replication, adeno origin of replication, AAV origin of replication, or BBV origin of replication, but is not limited thereto. The promoter in an expression vector for a eukaryotic host cell may be a promoter derived from genomes of mammalian cells (for example, a metallothionein promoter) or a promoter derived from mammalian viruses (for example, an adenovirus late promoter, a vaccinia virus 7.5K promoter, a SV40 promoter, a cytomegalovirus promoter, and a tk promoter of HSV), and the transcription termination sequence may have, in general, a polyadenylation sequence.

Another embodiment provides a recombinant cell comprising the recombinant vector.

The recombinant cell may be obtained by introducing the recombinant vector into a suitable host cell. The host cell, which is capable of stably and consecutively cloning or expressing the recombinant vector, may be any host cells known in the art. The prokaryotic cell may be *E. coli* JM109, *E. coli* BL21, *E. coli* RR1, *E. coli* LE392, *E. coli* B, *E. coli* X 1776, *E. coli* W3110, a *Bacillus* genus bacterial cell such as *Bacillus subtilis* or *Bacillus thuringiensis*, intestinal bacteria such as *Salmonella typhimurium*, *Serratia marcescens*, or various *Pseudomonas* species. A eukaryotic host cell may be a yeast (*Saccharomyce cerevisiae*), an insect cell, a plant cell, or an animal cell, for example, Sp2/0, CHO (Chinese hamster ovary) K1, CHO DG44, PER.C6, W138, BHK, COS-7, 293, HepG2, Huh7, 3T3, RIN, MDCK cell line and so on, but is not limited thereto.

The polynucleotide or the recombinant vector including the same may be transferred (introduced) into the host cell by using a method widely known in the art. For example, when a prokaryotic cell is used as the host cell, the transfer may be performed using a $CaCl_2$ method or an electroporation method, and when a eukaryotic cell is used as the host cell, the transfer may be performed by microinjection, calcium phosphate precipitation, electroporation, liposome-mediated transfection, or gene bombardment, but is not limited thereto.

The transformed host cell may be selected using a phenotype expressed by a selectable marker by known methods in the art. For example, when the selectable marker is a specific antibiotic resistance gene, a transformant is cultured in a medium containing the antibiotic, and thus the transformant may easily be selected.

Provided is an anti-Ang2 antibody for target-treating to Ang2, which, among the factors involved in neovascular formation and growth in a cancer tissue, has been drawing a new attention lately by the elucidation of its molecular mechanism, and it can be usefully developed as a new innovative antibody drug having excellent effects compared to the pre-existing antibody drugs. In addition, it is expected that the use of the anti-Ang2 antibody may be expanded to development of multi-specific antibody and the like.

Examples

Hereafter, the present disclosure will be described in detail by examples.

The following examples are intended merely to illustrate the invention and are not construed to restrict or limit the invention in any way.

Example 1

Preparation of an Anti-Ang2 Antibody

An anti-Ang2 antibody was prepared by inducing immune response through administering human Ang2 protein (R&D systems) together with and an adjuvant to 5-week old BALB/c mice, and then preparing hybridomas each of which produces each antibody according to a known method described in the paper written by Schwaber et al. (Schwaber, J and Cohen, E. P., "Human×Mouse Somatic Cell Hybrid Clones Secreting Immunoglobulins of Both Parental Types," Nature, 244 (1973), 444-447).

In particular, to obtain immunized mice necessary for preparing hybridoma cell lines, 100 μg of human Ang2 protein (R&D Systems) mixed with the same amount of a complete Freund's adjuvant was administered via an intraperitoneal injection to each of five 4-6-week-old BALB/c mice (Japan SLC, Inc.). After two weeks, the antigen (half of the previously injected amount) mixed with an incomplete Freund's adjuvant using the same method as described above was administered to each mouse via an intraperitoneal injection. After one additional week, a final boosting was performed and three days later, blood was collected from the tail of each mouse to obtain serum, which was then diluted at 1/1000 with PBS and subjected to an ELISA to verify that the titer of an antibody recognizing Ang2 was increased. From the results, mice in which a sufficient amount of the antibody was obtained were selected, and a cell fusion process was performed on the selected mice.

Three days before the cell fusion experiment, a mixture of 50 μg of PBS and 100 μg of human Ang2 protein (R&D systems) was administered via an intraperitoneal injection to BALB/c mice (Japan SLC, Inc.), and after each immunized mouse was anesthetized, its spleen located on the left side of the body was extracted. The extracted spleen was ground with a mesh to isolate cells, which were mixed with a culture medium (DMEM, Hyclon) to prepare a spleen cell suspension. The suspension was centrifuged to collect a cell layer. The obtained $1 \times 10^8$ spleen cells were mixed with $1 \times 10^7$ myeloma cells (Sp2/0), and the mixture was centrifuged to precipitate the cells. The centrifuged precipitate was slowly dispersed, treated with 1 ml of 45% polyethylene glycol (PEG 1500) contained in a culture medium (DMEM), and maintained at 37° C. for one minute before adding 1 ml of a culture medium (DMEM). Subsequently, 10 ml of the culture medium (DMEM) was added for 1 minute to the resultant, which was incubated in a water bath at 37° C. for 5 minutes and then re-centrifuged after the total volume was adjusted to 50 ml. The resulting cell precipitate was re-suspended in an isolation medium (HAT medium) at a concentration of $1 \sim 2 \times 10^5$/ml, and the resultant suspension was distributed at 0.1 ml to the each well of a 96-well plate, which was then incubated in a carbon dioxide incubator at 37° C. to prepare the hybridoma cell groups.

Example 2

Selection of Anti-Ang2 Antibody Producing Clone and Purification of Antibody The above obtained individual antibody producing hybridomas were screened using a typical ELISA format to select hybridomas which produce 95 anti-Ang2 monoclonal antibodies among the hybridomas differentiated from their mother hybridomas, based on their binding potential with Ang2.

More specifically, to select the hybridoma cells that specifically react only to Ang2 protein among the hybridoma cell groups prepared in Example 1 above, an ELISA assay method using a human Ang2 protein as an antigen was used for screening.

Human Ang-2 protein was added at 100 ng per well to a microtiter plate to be adhered to the surface of the plate, and unreacted antigens were removed by washing. 50 μl of the hybridoma cell culture obtained in Example 1 above was added to each well to react for 1 hour and then, the wells were sufficiently washed with phosphate buffered saline-TWEEN 20 (PBST) solution to remove unreacted culture solution. Goat anti-mouse IgG-horseradish peroxidase (goat anti-mouse IgG-HRP) was added thereto, a reaction was allowed to occur at a room temperature for 1 hour and then, washing was sufficiently performed with the TBST solution. Subsequently, substrate solution (OPD) of peroxidase was added to each well to react, and the reaction degree was measured by the absorption at 450 nm using an ELISA reader to repeatedly select hybridoma cell lines that secret antibodies having specifically high binding affinity only to human Ang2 protein. A limiting dilution was performed on the hybridoma cell lines obtained through repetitive selection to obtain final 58 clones of hybridoma cell lines producing monoclonal antibodies.

Each hybridoma obtained above was cultured in DMEM (Dulbeco's Modified Eagle's Medium) and then, the culture solutions were collected and subjected to Protein G-affinity chromatography method to purify anti-Ang2 monoclonal antibodies produced from each hybridoma.

First, the hybridoma cells cultured in 50 ml of culture medium (DMEM) containing 10% (v/v) FBS were centrifuged to obtain a cell precipitate, which was washed at least twice with 20 ml of PBS to remove the FBS. The cell precipitate was re-suspended in 50 ml of the culture medium (DMEM) and then incubated in a carbon dioxide incubator at 37° C. for 3 days. Subsequently, the cell culture was centrifuged to remove the antibody-producing cells, and the culture medium including the secreted antibodies was isolated and then, stored at 4° C. or used directly. Antibodies were purified from 50 to 300 ml of the culture medium using an AKTA purification device (GE Healthcare) equipped with an affinity column (protein G agarose column; Pharmacia, USA). The purified antibodies were stored for subsequent use after replacing the supernatant with PBS using a filter for protein aggregation (Amicon).

Example 3

Examination of Ang2:Tie-2 Binding Inhibition

In order to confirm whether the antibody binding to Ang2 prepared in Example 2 is a neutralizing antibody which actually inhibits the binding of Ang2 and Tie-2, Ang2-Tie2 binding competition ELISA was conducted using the antibody.

More specifically, MaxiSorp™ flat-bottom plate (Nunc) of 96-well was coated with hTie2-Fc (R&D Systems) which is a protein bound with 4 μg/ml of Fc of human IgG1. After coating, the plate was washed five times with 0.05% (v/v) Tween-20-containing PBS (phosphate buffer saline) and then blocked with 1% (v/v) BSA (bovine serum albumin; Sigma)-containing PBS at a room temperature for 2 hour.

For Ang2:Tie2 competition ELISA, each anti-Ang2 antibody obtained in Example 2 was placed at various concentrations of 400 nM-0.001 nM into each well coated with the hTie-2/Fc fusion protein along with 1% (v/v) BSA and 400 ng/ml of a FLAG-tagged hAng-2 and then, the plate was allowed to react at a room temperature for 2 hours and washed five times with PBST. After that, a HRP-conjugated anti-FLAG antibody (Sigma) diluted in 1% (v/v) BSA-containing PBS at a ratio of 1:5,000 (v/v) was added in an amount of 1000 to each well to react at a room temperature for 1 hour and then, the plate was washed five times with PBST. Lastly, 100 μl of TMB substrate (Cell Signaling) was added to each well of the plate to induce color development for 3 min. and then, the reaction was ceased by the addition of 100 μl of Stop solution (Cell Signaling) and OD450 values were measured on a plate reader (Molecular Devices).

From the obtained results, the concentration (50% inhibition concentration, IC50) where 50% of Ang2:Tie-2 binding is inhibited was obtained, which indicates that the anti-Ang2 antibody can neutralize the binding intensity between Ang2 and Tie-2. The obtained results are shown in Table 3:

TABLE 3

| Antibody | 50% inhibition concentration to Ang2:Tie-2 binding (IC50, nM) |
| --- | --- |
| SAIT-ANG2-AB-m1A10 | 1.34 |
| SAIT-ANG2-AB-m1B6 | 2.89 |
| SAIT-ANG2-AB-m3E2 | 0.55 |
| SAIT-ANG2-AB-m8D3 | 0.99 |

Example 4

Examination of Binding Affinity of an Anti-Ang2 Antibody to hAng2 and hAng1

To more exactly measure the binding affinity of the anti-Ang2 antibodies to antigen Ang2, the binding affinity of the above antibodies to the antigen was measured by an surface plasmon resonance (SPR) method using BIAcore T100 (GE Healthcare). The SPR method uses refractive index change of light which passes a sensor chip according to the state of materials coated onto the sensor chip, and if an antigen or an antibody is flowed onto a chip coated with the antigen or antibody, it causes changes in refractive index due to their binding and Kd values are thus calculated from the measured values.

First, anti-His antibody was immobilized on a CM5 sensor chip (GE healthcare) up to 8,000 RU levels using a pH 5.0 acetate solution and an amine coupling kit (GE Healthcare). 6 μg/ml of a recombinant hAng-2 (C-His, R&D Systems) protein was flowed onto the chip to be captured at 100 to 200 RU levels. The antibody obtained in Example 2 above was diluted serially twice each time starting from 100 nM concentration and it was each flowed onto the chip to allow it to be bound to (on), dissociated from (off), and regenerated (using 10 mM NaOH solution) from the antigen captured on the sensor chip, thereby measuring antigen-antibody affinity. With regard to hAng1, such experiments were conducted, and the results are as shown in the following Table 4.

TABLE 4

| Antibody | hAng2 (Kd, nM) | hAng1 (Kd, nM) |
|---|---|---|
| SAIT-ANG2-AB-m1A10 | 4.2 | No binding |
| SAIT-ANG2-AB-m1B6 | 2.3 | No binding |
| SAIT-ANG2-AB-m3E2 | 1.3 | No binding |
| SAIT-ANG2-AB-m8D3 | 4.0 | No binding |

The hybridomas producing the 4 antibodies were deposited in the Korean Cell Line Bank located at Yongon-dong, Chongno-gu, Seoul, South Korea, as of Dec. 20, 2013 and received accession numbers KCLRF-BP-00305 (SAIT-ANG2-AB-m3E2), KCLRF-BP-00306 (SAIT-ANG2-AB-m1A10), KCLRF-BP-00307 (SAIT-ANG2-AB-m1B6), and KCLRF-BP-00308 (SAIT-ANG2-AB-m8D3), respectively.

Example 5

Examination of Binding Affinity of an Anti-Ang2 Antibody to mAng2

An ELISA was conducted to measure the binding affinity of the antibodies prepared in Example 2 to mouse Ang2 (mAng2). MaxiSorp™ flat-bottom plate (Nunc) of 96-well was coated with 5-20 μg/ml of mouse Ang2 (Mouse Ang2; Accession # NP_031452) (R&D Systems). Thereafter, the plate was washed five times with 0.05% (v/v) Tween-20-containing PBS (PBST) and then blocked with 1% (v/v) BSA (bovine serum albumin; Sigma)-containing PBS at a room temperature for 2 hour. Each of the anti-Ang2 antibodies was added to each well of the plate at various concentrations, and the plate was allowed to react at a room temperature for 2 hours.

Thereafter, the plate was washed five times with PBST. Then, a HRP-conjugated anti-mouse IgG antibody (Santacruz) diluted in 1% (v/v) BSA-containing PBS at a ratio of 1:1,000 (v/v) was added in an amount of 50 μl to each well to react at a room temperature for 1 hour and then, the plate was washed five times with PBST. Lastly, 100 μl of TMB substrate (Cell Signaling) was added to each well of the plate to induce color development for 3 min. and then, the reaction was ceased by the addition of 100 μl of Stop solution (Cell Signaling) and OD450 values were measured on a plate reader (Molecular Devices).

From the obtained results, 50% binding concentration (Kd) of the anti-Ang2 antibody to Ang2 protein is obtained, thereby measuring the binding intensity of each of the anti-Ang2 antibodies to Ang2. The obtained results are shown in Table 5:

TABLE 5

| Antibody | mAng2 (Kd, nM) |
|---|---|
| SAIT-ANG2-AB-m1A10 | No binding |
| SAIT-ANG2-AB-m1B6 | 2.1 |
| SAIT-ANG2-AB-m3E2 | 130 |
| SAIT-ANG2-AB-m8D3 | 141 |

Example 6

Identification of Antigen Recognition Region (Epitope) of the Anti-Ang2 Antibodies To identify the epitope for each of the anti-Ang2 antibodies obtained in Example 2, ELISA was performed using a recombinant protein wherein receptor binding site of Ang2 protein is tagged with Flag or an artificial mutation is introduced into full-length Ang2.

A 96-well MaxiSorp™ flat-bottom plate (Nunc) was coated with 50 μl of each anti-Ang2 antibody (400 nM). After that, the plate was washed five times with 0.05% (v/v) Tween-20-containing PBS (PBST) and then blocked with 1% (v/v) BSA-containing PBS at a room temperature for 2 hours. S417, P419, N421, I434, D448, A449, P452, Y460, N467, K468, or F469 residue of Ang2 (SEQ ID NO: 27) was mutated (substituted) with alanine and tagged with FLAG (N-DYKDDDDK-C; 1012 Da) and then 250 ng of them was each added to each well to the plate, which was allowed to react at a room temperature for 2 hours.

Thereafter, the plate was washed five times with 0.05% (v/v) Tween-20-containing PBS and then, an HRP-conjugated anti-FLAG antibody (SIGMA) diluted in 1% (v/v) BSA-containing PBS at 1:5,000 ratio (v/v) was added in the amount of 50 μl to each well to react at a room temperature for 1 hour, followed by washing five times with 0.1% (v/v) Tween-20-containing PBS.

Finally, 100 μl of TMB substrate (cell signal) was added to each well of the plate to induce color development for 3 minutes and then, the reaction was ceased by the addition of 100 μl of stop solution (Cell signaling) and OD450 values were measured on a plate reader (Molecular Devices). By comparing binding intensity to mutated Ang2 to binding intensity to non-mutated (native) Ang2, each epitope for the Ang2 antibodies was identified. The obtained binding intensity (%) (binding intensity to mutant Ang2/binding intensity to native Ang2) was shown in Tables 6 and FIG. 1.

Table 6

| | Binding (%) | | | | | | | | | | | |
|---|---|---|---|---|---|---|---|---|---|---|---|---|
| | Loop 1 | | | | Loop 2 | | | | Loop 3 | | | Loop4 |
| RBD mutant | S417 | Q418 | P419 | N421 | I434 | D448 | A449 | P452 | Y460 | N467 | K468 | F469 |
| 1A10 | 99.96 | 97.2 | 101.6 | 89.3 | 93.2 | 95.3 | 95.6 | 104.7 | 8.3 | 79.4 | 27.3 | 77.9 |
| Ang2 mutant | — | — | — | — | I434 | — | — | — | — | — | K468 | F469 |
| 8D3 | | | | | 137.3 | | | | | | 20.5 | 41.9 |

(In Table 6, "RBD mutant" refers to a mutant prepared using the receptor binding domain (amino acid residues from $276^{th}$ to $496^{th}$ positions) of Ang2;

"1A10" and "8D3" refer to "SAIT-ANG2-AB-m1A10" and "SAIT-ANG2-AB-m8D3", respectively)

As shown in Table 6, the binding intensities to mutant Ang2, Y460 and K468, are decreased as 30% or less of that to native Ang2.

Example 7

Examination of Ang2 Receptor Activity Inhibition by Ang2 Antibodies

As Ang2 induces a change in vascular endothelial cells by binding to a Tie2 receptor expressed in the vascular endothelial cells to induce the phosphorylation of the receptor and activate it, the Ang2 inhibitory activities of the anti-Ang2 antibodies were verified through the functional analysis of the antibodies using a cell-based assay.

For this, $1 \times 10^6$ of Tie2-overexpressed CHO (Chinese hamster ovary) cell (Kim et al., *Biochim Bioohys Acta.*, 2009) were cultured in a 60 mm culture dish using 5% (v/v) FBS (Gibco)-containing IMDM media (Gibco) at 37° C. and when they reached 80~90% confluency, the media were replaced with serum-free IMDM media and further cultured at 37° C. for 16 hours. The dish was washed once with PBS and after the replacement with 0.1 nM sodium orthovanadate-mixed IMDM media, they were further cultured for 10 min. After washed once with PBS, the cultured cells were treated with a mixture prepared by mixing the anti-Ang2 antibodies prepared in Example 2 at various concentrations with 20 nM human Ang2 protein (R&D systems) and letting them stand for 20 min, and further cultured for 10 min.

The cells were washed using a cold PBS, treated with 300 μl of lysis buffer (Roche), collected to a tube to allow them to be dissolved at 4° C. for 30 minutes, and then, centrifuged at 13,000 rpm for 15 minutes to quantify a supernatant. 2 μg of anti Tie2 antibody (R&D system) was added to 0.5 mg of a cell lysate, which was then overnight reacted at 4° C. and then subjected to immunoprecipitation by the addition of protein A bead (GE Healthcare) thereto.

The reactant obtained above was centrifuged at 13,000 rpm for 15 minutes to obtain a pellet, which was washed two to three times with lysis buffer (Roche). A sample buffer (Invitrogen) mixed with a reducing agent was added thereto. The obtained mixture was boiled at 95° C. for 5 minutes, and then, applied to NuPAGE Novex 4-12% Bis-Tris gel (Invitrogen) and transferred onto Nitrocellulose membrane (Invitrogen).

To verify the presence of the phosphorylation of Tie2, the above blots were blocked with PBST mixed with 3% (v/v) skim milk (Sigma) for 30 minutes and identified using an HRP-conjugated anti-phospho tyrosine antibody (Millipore). For Tie2 identification, the blots were reacted in a stripping buffer (Thermo) for 15 minutes and then blocked again and identified using an anti Tie2 antibody (Santa cruz). After band intensities were measured using Image J software (http://rsb.info.nih.gov/ij/index.html), the inhibitory degrees of Tie2 phosphorylation after the treatment of the anti-Ang2 antibodies were calculated in relative % against the Ang2 single treatment group, and the results are shown in the following Table 7 and FIG. 2.

TABLE 7

| Antibody (treated amount: 50 nM) | Tie2 phosphorylation inhibition (%) |
|---|---|
| SAIT-ANG2-AB-m1A10 | 82.01% |
| SAIT-ANG2-AB-m3E2 | 76.89% |
| SAIT-ANG2-AB-m8D3 | 76.69% |

Figure 2:
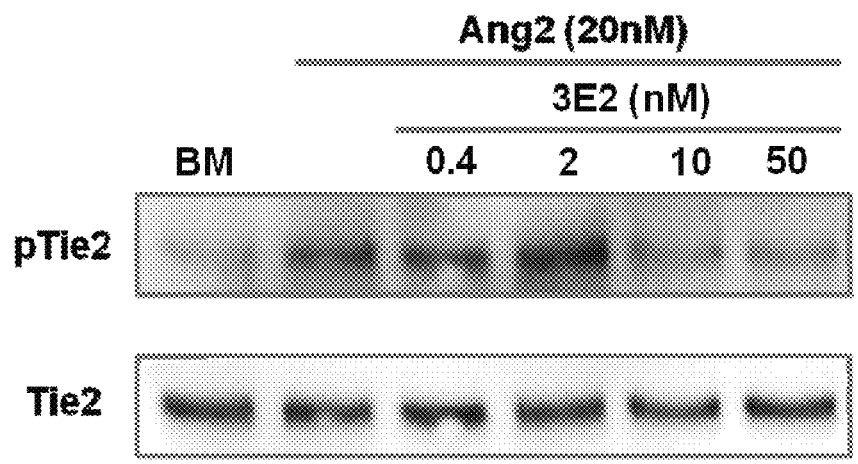
FIG. 2 is an image of an immunoblot showing the degree of Tie2 phosphorylation by administering an anti-Ang2 antibody.

As shown in Table 7 and FIG. 2, the anti-Ang2 antibodies can effectively inhibit the phosphorylation of Tie2.

Example 8

Inhibition of Cell Migration by Anti-Ang2 Antibodies

To confirm whether the above prepared anti-Ang2 antibody can inhibit the migration of vascular endothelial cells, an assay using Oris cell migration kit (Platypus technology) was performed.

Vascular endothelial cells (Human umbilical vein endothelial cells (HVUEC), ATCC) were sub-confluently cultured in EGM-2 medium (Lonza). $2.5 \times 10^4$ cells of the cultured HVUEC were seeded onto each well of a migration plate equipped with a stopper, and cultured for 24 hours. The stopper was removed from the confluently cultured cells, to make cell free zone, and then, the plate was washed once with PBS.

Figure 3:
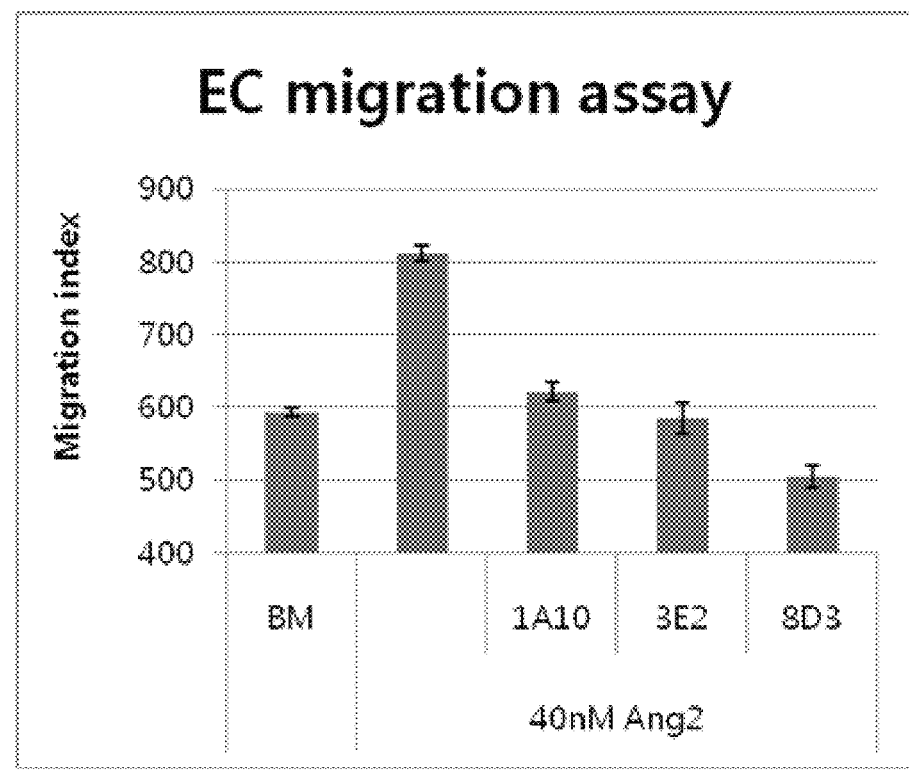
FIG. 3 is a graph showing the degree of vascular endothelial cell migration during administration of an anti-Ang2 antibody.
Figure 4:
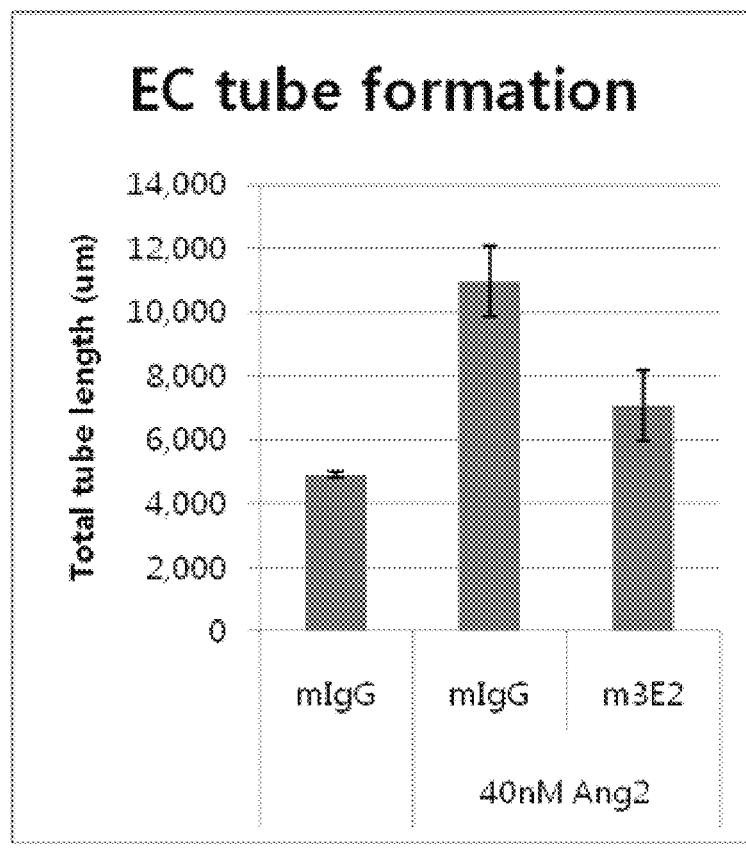
FIG. 4 is a graph showing the total length of vascular endothelial cell tube formation during administration of an anti-Ang2 antibody.

Various concentrations of each of the anti-Ang2 antibodies prepared in Example 2 were mixed with 40 nM Ang2 protein (R&D systems) in serum-free medium, and allowed to be reacted for 20 minutes. The cultured cells were treated with the reactant and further cultured for 24 hours. A mixture where Calcein (BD) was mixed with serum-free medium to the concentration of 8 μg/ml was added to each well at the amount of 5 μl, and left for reaction for 30 minutes, to stain the cells. Thereafter, a blocker was equipped in the back of the plate, and fluorescence images were obtained using InCell analyzer6000 (GE Healthcare). Then, the fluorescence intensity in migration zone was quantified, and shown in FIG. 3 as migration index. As shown in FIG. 3, the anti-Ang2 antibody effectively inhibits the cell migration.

Example 9

Inhibition of In Vitro Vasculogenesis by Anti-Ang2 Antibodies

To confirm whether the prepared anti-Ang2 antibodies can inhibit tube formation of vascular endothelial cells by Ang2, HUVEC tube formation assay was performed.

Vascular endothelial cells (Human umbilical vein endothelial cells (HVUEC), ATCC) were sub-confluently cultured in EGM-2 medium (Lonza). After replacement with serum-free medium, the cells were further cultured for 6 hours. 200 nM of each of the anti-Ang2 antibodies prepared in Example 2 was mixed with 80 nM Ang2 protein (R&D systems) in serum-free medium, and the obtained mixture was mixed with $8 \times 10^5$ cells/ml of HVUEC suspension at the ratio of 1:1. 50 μl of the obtained mixture was seeded into each well of Matrigel-coated 96-well plate (BD BioCoat Angiogenesis System-Endothelial Cell Tube Formation) and cultured for 18 hours. Thereafter, and 50 μl of a mixture, where calcein (BD) was mixed with serum-free medium to the concentration of 8 m/ml, was added to each well and left for reaction for 30 minutes, to stain the cells. Fluorescence images were obtained using a fluorescence microscope (Zeiss). From the images, the length of the formed tube was measured using AxioVision (Zeiss) and the sum thereof is shown in FIG. 4.

Example 10

Inhibition of Colo205 Tumor Cell Growth by Anti-Ang2 Antibodies

Figure 5A:
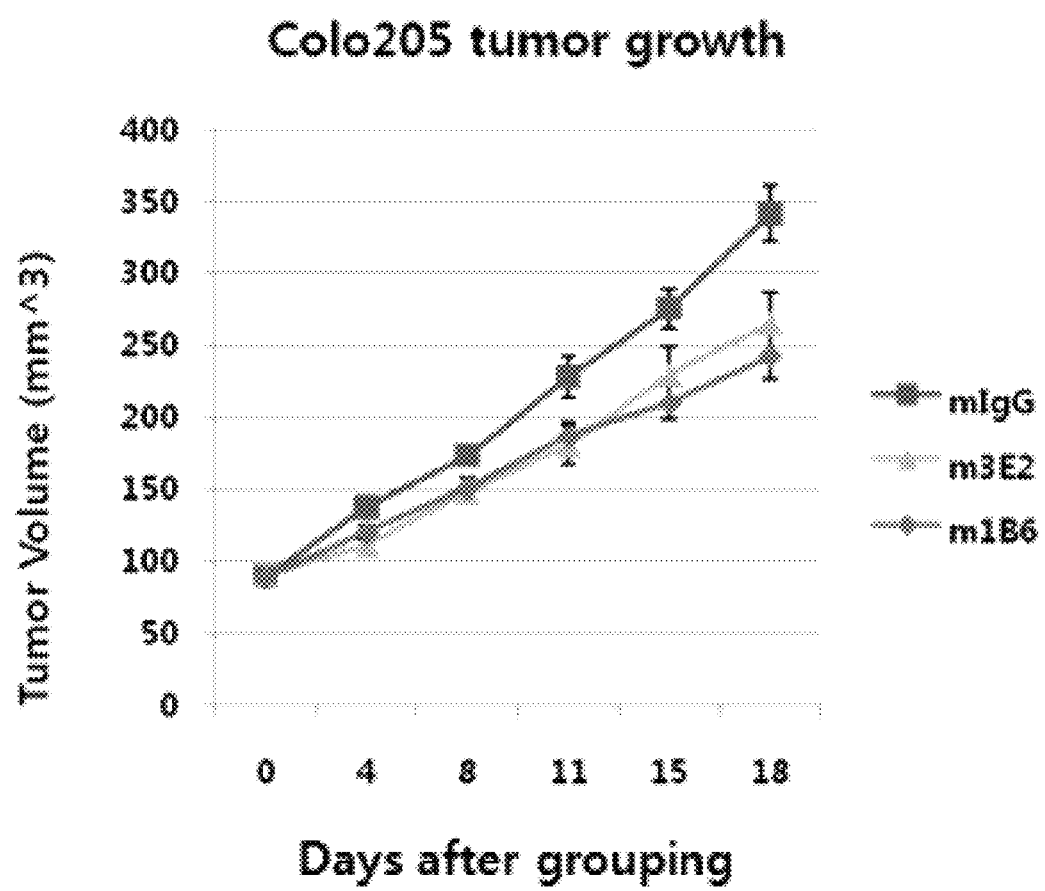
FIG. 5A is a graph showing a volume change of colorectal cancer cells by administering an anti-Ang2 antibody according to the days of administration (x axis: day after grouping).
Figure 5B:
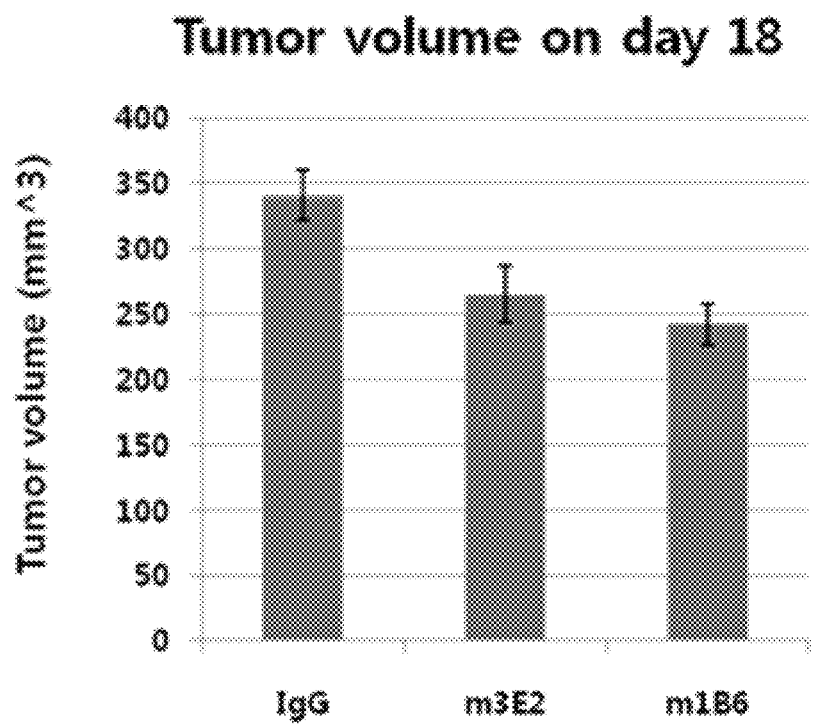
FIG. 5B is a graph showing a volume change of colorectal cancer cells at $18^{th}$ day of administering an anti-Ang2 antibody according to the kind of antibodies administered.

To verify the tumor cell growth inhibition effect of the anti-Ang2 antibodies, an experiment was performed for a colorectal cancer cell xenograft model using human colorectal cancer cell line Colo205 (ATCC). Colo205 cells were cultured in 10% (v/v) FBS (Gibco)-containing RPMI-1640 medium (Gibco). $5 \times 10^5$ cells of the cultured Colo205 cells were re-suspended in 100 µl of serum-free medium, and administered via subcutaneous injection using 1~2% (v/v) isoflurane to anesthetized BALB/c nude mice (4~5 weeks old; Shanghai SLAC Laboratory Animal Co. Ltd.). When the size of the tumor reaches 100~200 mm$^3$, each of the anti-Ang2 antibodies prepared in Example 2 was administered via intraperitoneal injection at the concentration of 10 mg/kg twice a week, and then the tumor size was measured. The tumor size (V) was calculated by the following formula: V=(length×width$^2$)/2. The obtained results are shown in FIG. 5A (change in the tumor size according to administration days) and FIG. 5B (the tumor size at day 18 according to the kind of the antibodies). X axis in FIG. 5A shows days after grouping, which refers to the number of antibody administration days.

Example 11

Gene Cloning of Anti-Ang2 Antibodies

Total RNA was obtained from each of the prepared antibody producing hybridomas ($2 \times 10^6$ cells) using RNeasy mini kit (Qiagen). Then, using the RNA as a template, gene sequences of a heavy chain variable region and light chain variable region were amplified from a monoclonal antibody produced from each of the hybridomas using OneStep RT-PCR kit (Qiagen), Mouse Ig-Primer Set (Novagen) and thermocycler (GeneAmp PCR System 9700, Applied Biosystem): at 94° C. for 5 minutes; [at 50° C. for 30 minutes and at 95° C. for 15 minutes], [at 94° C. for 1 minute, at 50° C. for 1 minute, and 72° C. for 2 minutes]×35 cycles; at 72° C. for 6 minutes; cooled to 4° C.

The PCR product obtained from each of the above reactions was subjected to direct DNA sequencing, to obtain sequences of CDRs, heavy chain variable region and light chain variable region of each antibody. The obtained sequences of CDRs, heavy chain variable region and light chain variable region of each antibody are shown in Table 8 (heavy chain CDRs), Table 9 (light chain CDRs), and Table 10 (heavy chain variable region and light chain variable region).

TABLE 8

Amino acid sequence of heavy chain CDRs

| Antibody | CDRH1-KABAT | CDRH2-KABAT | CDRH3-KABAT |
|---|---|---|---|
| SAIT-ANG-2-AB-m1A10 | SYWLE (SEQ ID NO: 1) | EILPGSGSTNYNEKFRG (SEQ ID NO: 5) | GNHNSYYYAMDY (SEQ ID NO: 9) |
| SAIT-ANG-2-AB-m8D3 | DYYMK (SEQ ID NO: 2) | EINPKNGDTFYNQIFKG (SEQ ID NO: 6) | ENDYDVGFFDY (SEQ ID NO: 10) |
| SAIT-ANG-2-AB-m1B6 | NYGMN (SEQ ID NO: 3) | WINTYTGEPTYADDFKG (SEQ ID NO: 7) | DHDGYLMDY (SEQ ID NO: 11) |
| SAIT-ANG-2-AB-m3E2 | DPYIH (SEQ ID NO: 4) | RIDPANGNTKYDPKFQG (SEQ ID NO: 8) | RWDGGGFDY (SEQ ID NO: 12) |

TABLE 9

Amino acid sequence of light chain CDRs

| Antibody | CDRL1-KABAT | CDRL2-KABAT | CDRL3-KABAT |
|---|---|---|---|
| SAIT-ANG-2-AB-m1A10 | RASESVDSYGNSFMH (SEQ ID NO: 13) | RASNLDS (SEQ ID NO: 17) | QQSNEDPLT (SEQ ID NO: 21) |
| SAIT-ANG-2-AB-m8D3 | KASQSVSNDVA (SEQ ID NO: 14) | YASNRYP (SEQ ID NO: 18) | QQDYTSPWT (SEQ ID NO: 22) |
| SAIT-ANG-2-AB-m1B6 | STSQGISNYLN (SEQ ID NO: 15) | YTSSLHS (SEQ ID NO: 19) | QQYSKLPYT (SEQ ID NO: 23) |
| SAIT-ANG-2-AB-m3E2 | RASQDISNYLN (SEQ ID NO: 16) | YTSRLHS (SEQ ID NO: 20) | QQGNTLPWT (SEQ ID NO: 24) |

TABLE 10

| | Heavy chain variable region | Light chain variable region |
|---|---|---|
| SAIT-ANG-2-AB-m1A10 | QVQLQQSGAELMKPGASVKISCKATDY<br>TFSSYWLEWLIQRPGHGLEWIGEILPGS<br>GSTNYNEKFRGKATFTEDTSSNTAYMQ<br>LSSLTSEDSAVYYCARGNHNSYYYAMD<br>YWGQGTSVTVSS (SEQ ID NO: 28)<br>caggttcagctgcagcagtctggagctgagctgatgaagcct<br>ggggcctcagtgaagatatcctgcaaggctactgactacacat<br>tcagtagctactggctagagtggttaatacagaggcctggaca<br>tggccttgagtggattggagagatatacctggaagtggtagta<br>ctaactacaatgagaagttcaggggcaaggccacattcactg<br>aagatacatcctccaacacagcctacatgcaactcagcagcct<br>gacatctgaggactctgccgtctattactgtgcaagaggtaac<br>cacaactcctattactatgctatggactactggGGTCAAG<br>GAACCTCAGTCACCGTCTCCTCA (SEQ ID NO: 32) | DIVLTQSPASLAVSLGQRATISCRASES<br>VDSYGNSFMHWYQQKPGQPPKLLIYR<br>ASNLDSGIPARFSGSGSRTDFTLTINPVE<br>ADDVATYYCQQSNEDPLTFGAGTKLEL<br>K (SEQ ID NO: 36)<br>gacattgtgctgacccaatctccagcttctctggctgtgtctcta<br>ggtcagagggccaccatatcctgcagagccagtgaaagtgtt<br>gatagttatggcaatagttttatgcactggtaccagcagaaac<br>caggacagccacccaaactcctcatctatcgtgcatccaacct<br>agattctgggatccctgccaggttcagtggcagtgggtctag<br>gacagacttcaccctcaccattaatcctgtggaggctgatgat<br>gttgcaacctattactgtcagcaaagtaatgaggatcctctcac<br>gttcggtgctgggaccaagctggagctgaaa (SEQ ID NO: 40) |
| SAIT-ANG-2-AB-m8D3 | EVQLQQSGPELVKPGDSVKMSCKASGY<br>TFTDYYMKWVRQSHGKSLQWVGEINP<br>KNGDTFYNQIFKGKATLTVDKSSSTAY<br>MQLTSLTSEDSAVYYCTRENDYDVGFF<br>DYWGQGTSVTVSS (SEQ ID NO: 29)<br>Gaggtccagctgcaacagtctggacctgagctggtgaagcc<br>tggggattcagtgaagatgtcctgcaaggcttctggatacacct<br>tcactgactactacatgaagtgggtgaggcagagccatggaa<br>agagccttcagtgggtggagaaattaatcctaagaatggtgat<br>actttctacaaccagatattcaagggcaaggccacattgactgt<br>agacaaatcctccagcacagcctacatgcaactcaccagcct<br>gacatctgaggactctgcagtctattactgtacacgtgagaatg<br>attacgacgtgggattctttgactactggGGTCAAGGA<br>ACCTCAGTCACCGTCTCCTCA (SEQ ID NO: 33) | TIVMTQTPKFLLVSAGDRITITCKASQS<br>VSNDVAWYQQKPGQSPKLLIYYASNR<br>YPGVPDRFTGSGYGTDFTFTISTVQAED<br>LAVYFCQQDYTSPWTFGGGTELEIK<br>(SEQ ID NO: 37)<br>ActattgtgatgacccagactcccaaattcctgCttgtatcag<br>caggagacaggattaccataacctgcaaggccagtcagagt<br>gtgagtaatgatgtagcctggtatcaacagaagccagggca<br>gtctcctaaactgctgatatactatgcatccaatcgctaccctg<br>gagtccctgatcgcttcactggcagtggatatgggacggattt<br>cactttcaccatcagcactgtgcaggctgaagacctggcagtt<br>tatttctgtcagcaggattatacctccgtggacgttcggtgg<br>aggcaccgagctggaaatcaaa (SEQ ID NO: 41) |
| SAIT-ANG-2-AB-m1B6 | QIQLVQSGPELKKPGETVKISCKASGYT<br>FTNYGMNWVKQAPGKGLKWMGWINT<br>YTGEPTYADDFKGRFAFSLETSASTAYL<br>QINNLKNEDTATYFCARDHDGYLMDY<br>WGQGTSVTVSS (SEQ ID NO: 30)<br>cagatccagttggtgcagtctggacctgagctgaagaagcct<br>ggagagacagtcaagatctcctgcaaggcttctggatatacct<br>tcacaaactatggaatgaactgggtgaagcaggctccaggaa<br>agggtttaaagtggatgggctggataaacacctacactggag<br>agccaacatatgctgatgacttcaagggacgttttgccttctctt<br>ggaaacctctgccagcactgcctatttgcagatcaacaacctc<br>aaaaatgaggacacggctacatatttctgtgcaagagatcatg<br>atggttaccttatggactactggGGTCAAGGAACCT<br>CAGTCACCGTCTCCTCA (SEQ ID NO: 34) | DIQMTQTTSSLSASLGDRVTISCSTSQGI<br>SNYLNWYQQKPDGTVKLLIFYTSSLHS<br>GVPSRFSGSGSGTDYSLTISNLEPEDIAT<br>YYCQQYSKLPYTFGGGTKLEIK (SEQ ID NO: 38)<br>Gatatccagatgacacagactacatcctccctgtctgcctctc<br>tgggagacagagtcaccatcagttgtagtacaagtcagggca<br>ttagcaattatttgaactggtatcagcagaaaccagatggaact<br>gttaaactcctgatcttttacacatcaagtttacactcaggagtc<br>ccatcaaggttcagtggcagtgggtctgggactgattattctct<br>caccatcagcaacctggaacctgaagatattgccacttactatt<br>gtcagcagtatagtaagcttccgtacacgttcgggggggga<br>ccaagctggaaataaaa (SEQ ID NO: 42) |
| SAIT-ANG-2-AB-m3E2 | EVQLQQSGAELVKPGASVKLSCTASGF<br>NIKDPYIHWVKQRPEQGLEWIGRIDPAN<br>GNTKYDPKFQGKATITADTSSNTAYLQ<br>LSSLTSEDTAVYYCVRRWDGGGFDYW<br>GQGTSVTVSS (SEQ ID NO: 31)<br>gaggttcagctgcagcagtctggggcagagcttgtgaagcca<br>ggggcctcagtcaagttgtcctgcacagcttctggcttcaacat<br>taaagaccccctatatacactgggtgaaacagaggcctgaaca<br>gggcctggagtggattggaaggattgatcctgcagggtaat<br>actaaatatgacccgaagttccagggcaaggccactataacg<br>gcagacacatcctccaacacagcctacctccagctcagcagc<br>ctgacatctgaggacactgccgtctattactgtgttagaaggtg<br>ggacggggggggattgactactggGGTCAAGGAA<br>CCTCAGTCACCGTCTCCTCA (SEQ ID NO: 35) | DIQMTQTTSSLSASLGDRVTISCRASQD<br>ISNYLNWYQQKPDGTVKLLIYYTSRLH<br>SGVPSRFSGSGSGTDYSLTITNLEQEDIA<br>TYFCQQGNTLPWTFGGGTKLEIK (SEQ ID NO: 39)<br>gatatccagatgacacagactacatcctccctgtctgcctctct<br>gggagacagagtcaccatcagttgcagggcaagtcaggac<br>attagcaattatttaaactggtatcagcagaaaccagatggaa<br>ctgttaaactcctgatctactacacatcaagattacactcagga<br>gtcccatcaaggttcagtggcagtgggtctggaacagattatt<br>ctctcaccattaccaacctggagcaagaagatattgccactta<br>cttttgccaacagggtaatacgcttccgtggacgttcggtgga<br>ggcaccaagctggaaatcaaa (SEQ ID NO: 43) |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An anti-Ang2 antibody or an antigen-binding fragment thereof, comprising
    a heavy chain variable region comprising a polypeptide (CDR-H1) comprising SEQ ID NO: 4, a polypeptide (CDR-H2) comprising SEQ ID NO: 8, and a polypeptide (CDR-H3) comprising SEQ ID NO: 12; and
    a light chain variable region comprising a polypeptide (CDR-L1) comprising SEQ ID NO: 16, a polypeptide (CDR-L2) comprising SEQ ID NO: 20, and a polypeptide (CDR-L3) comprising SEQ ID NO: 24.

2. The anti-Ang2 antibody or an antigen-binding fragment thereof of claim 1, wherein the antibody or antigen binding fragment thereof comprises a heavy chain variable region comprises the amino acid sequence of SEQ ID NO: 31, and a light chain variable region comprises the amino acid sequence of SEQ ID NO: 39.

3. A hybridoma of KCLRF-BP-00305.

4. A method of treating a colorectal cancer in a subject, comprising administering the anti-Ang2 antibody or an antigen-binding fragment thereof of claim 1 to the subject.

* * * * *

SEQUENCE LISTING

```
<160> NUMBER OF SEQ ID NOS: 43

<210> SEQ ID NO 1
<211> LENGTH: 5
<212> TYPE: PRT
<213> ORGANISM: Artificial Sequence
<220> FEATURE:
<223> OTHER INFORMATION: Synthetic CDR-H1 (e.g., for
      SAIT-ANG-2-AB-m1A10)

<400> SEQUENCE: 1

Ser Tyr Trp Leu Glu
  1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic CDR-H1 (e.g., for
      SAIT-ANG-2-AB-m8D3)

<400> SEQUENCE: 2

Asp Tyr Tyr Met Lys
  1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic CDR-H1 (e.g., for
      SAIT-ANG-2-AB-m1B6)

<400> SEQUENCE: 3

Asn Tyr Gly Met Asn
  1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic CDR-H1 (e.g., for
      SAIT-ANG-2-AB-m3E2)

<400> SEQUENCE: 4

Asp Pro Tyr Ile His
  1               5

<210> SEQ ID NO 5
<211> LENGTH: 17
<212> TYPE: PRT
```

<213> ORGANISM: Artificial Sequence
<220> FEATURE:
<223> OTHER INFORMATION: Synthetic CDR-H2 (e.g., for
      SAIT-ANG-2-AB-m1A10)

<400> SEQUENCE: 5

Glu Ile Leu Pro Gly Ser Gly Ser Thr Asn Tyr Asn Glu Lys Phe Arg
 1               5                  10                  15

Gly

<210> SEQ ID NO 6
<211> LENGTH: 17
<212> TYPE: PRT
<213> ORGANISM: Artificial Sequence
<220> FEATURE:
<223> OTHER INFORMATION: Synthetic CDR-H2 (e.g., for
      SAIT-ANG-2-AB-m8D3)

<400> SEQUENCE: 6

Glu Ile Asn Pro Lys Asn Gly Asp Thr Phe Tyr Asn Gln Ile Phe Lys
 1               5                  10                  15

Gly

<210> SEQ ID NO 7
<211> LENGTH: 17
<212> TYPE: PRT
<213> ORGANISM: Artificial Sequence
<220> FEATURE:
<223> OTHER INFORMATION: Synthetic CDR-H2 (e.g., for
      SAIT-ANG-2-AB-m1B6)

<400> SEQUENCE: 7

Trp Ile Asn Thr Tyr Thr Gly Glu Pro Thr Tyr Ala Asp Asp Phe Lys
 1               5                  10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: Synthetic CDR-H2 (e.g., for
      SAIT-ANG-2-AB-m3E2)

<400> SEQUENCE: 8

Arg Ile Asp Pro Ala Asn Gly Asn Thr Lys Tyr Asp Pro Lys Phe Gln
 1               5                  10                  15

Gly

<210> SEQ ID NO 9
<211> LENGTH: 12
<212> TYPE: PRT
<213> ORGANISM: Artificial Sequence
<220> FEATURE:
<223> OTHER INFORMATION: Synthetic CDR-H3 (e.g., for
      SAIT-ANG-2-AB-m1A10)

<400> SEQUENCE: 9

Gly Asn His Asn Ser Tyr Tyr Tyr Ala Met Asp Tyr
 1               5                  10

<210> SEQ ID NO 10
<211> LENGTH: 11
<212> TYPE: PRT
<213> ORGANISM: Artificial Sequence

```
<220> FEATURE:
<223> OTHER INFORMATION: Synthetic CDR-H3 (e.g., for
      SAIT-ANG-2-AB-m8D3)

<400> SEQUENCE: 10

Glu Asn Asp Tyr Asp Val Gly Phe Phe Asp Tyr
 1               5                  10

<210> SEQ ID NO 11
<211> LENGTH: 9
<212> TYPE: PRT
<213> ORGANISM: Artificial Sequence
<220> FEATURE:
<223> OTHER INFORMATION: Synthetic CDR-H3 (e.g., for
      SAIT-ANG-2-AB-m1B6)

<400> SEQUENCE: 11

Asp His Asp Gly Tyr Leu Met Asp Tyr
 1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic CDR-H3 (e.g., for
      SAIT-ANG-2-AB-m3E2)

<400> SEQUENCE: 12

Arg Trp Asp Gly Gly Gly Phe Asp Tyr
 1               5

<210> SEQ ID NO 13
<211> LENGTH: 15
<212> TYPE: PRT
<213> ORGANISM: Artificial Sequence
<220> FEATURE:
<223> OTHER INFORMATION: Synthetic CDR-L1 (e.g., for
      SAIT-ANG-2-AB-m1A10)

<400> SEQUENCE: 13

Arg Ala Ser Glu Ser Val Asp Ser Tyr Gly Asn Ser Phe Met His
 1               5                  10                  15

<210> SEQ ID NO 14
<211> LENGTH: 11
<212> TYPE: PRT
<213> ORGANISM: Artificial Sequence
<220> FEATURE:
<223> OTHER INFORMATION: Synthetic CDR-L1 (e.g., for
      SAIT-ANG-2-AB-m8D3)

<400> SEQUENCE: 14

Lys Ala Ser Gln Ser Val Ser Asn Asp Val Ala
 1               5                  10

<210> SEQ ID NO 15
<211> LENGTH: 11
<212> TYPE: PRT
<213> ORGANISM: Artificial Sequence
<220> FEATURE:
<223> OTHER INFORMATION: Synthetic CDR-L1 (e.g., for
      SAIT-ANG-2-AB-m1B6)

<400> SEQUENCE: 15

Ser Thr Ser Gln Gly Ile Ser Asn Tyr Leu Asn
 1               5                  10
```

```
<210> SEQ ID NO 16
<211> LENGTH: 11
<212> TYPE: PRT
<213> ORGANISM: Artificial Sequence
<220> FEATURE:
<223> OTHER INFORMATION: Synthetic CDR-L1 (e.g., for
      SAIT-ANG-2-AB-m3E2)

<400> SEQUENCE: 16

Arg Ala Ser Gln Asp Ile Ser Asn Tyr Leu Asn
 1               5                  10

<210> SEQ ID NO 17
<211> LENGTH: 7
<212> TYPE: PRT
<213> ORGANISM: Artificial Sequence
<220> FEATURE:
<223> OTHER INFORMATION: Synthetic CDR-L2 (e.g., for
      SAIT-ANG-2-AB-m1A10)

<400> SEQUENCE: 17

Arg Ala Ser Asn Leu Asp Ser
 1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic CDR-L2 (e.g., for
      SAIT-ANG-2-AB-m8D3)

<400> SEQUENCE: 18

Tyr Ala Ser Asn Arg Tyr Pro
 1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic CDR-L2 (e.g., for
      SAIT-ANG-2-AB-m1B6)

<400> SEQUENCE: 19

Tyr Thr Ser Ser Leu His Ser
 1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic CDR-L2 (e.g., for
      SAIT-ANG-2-AB-m3E2)

<400> SEQUENCE: 20

Tyr Thr Ser Arg Leu His Ser
 1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic CDR-L3 (e.g., for
      SAIT-ANG-2-AB-m1A10)
```

```
-continued

<400> SEQUENCE: 21

Gln Gln Ser Asn Glu Asp Pro Leu Thr
  1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic CDR-L3 (e.g., for
      SAIT-ANG-2-AB-m8D3)

<400> SEQUENCE: 22

Gln Gln Asp Tyr Thr Ser Pro Trp Thr
  1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic CDR-L3 (e.g., for
      SAIT-ANG-2-AB-m1B6)

<400> SEQUENCE: 23

Gln Gln Tyr Ser Lys Leu Pro Tyr Thr
  1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic CDR-L3 (e.g., for
      SAIT-ANG-2-AB-m3E2)

<400> SEQUENCE: 24

Gln Gln Gly Asn Thr Leu Pro Trp Thr
  1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic CDR-L2
<220> FEATURE:
<221> NAME/KEY: misc_feature
<222> LOCATION: (1)
<223> OTHER INFORMATION: Xaa is arginine (R) or tyrosine (Y)
<220> FEATURE:
<221> NAME/KEY: misc_feature
<222> LOCATION: (2)
<223> OTHER INFORMATION: Xaa is alanine (A) or threonine (T) (e.g., A)
<220> FEATURE:
<221> NAME/KEY: misc_feature
<222> LOCATION: (4)
<223> OTHER INFORMATION: Xaa is asparagine (N), arginine (R), or serine
      (S) (e.g., N)
<220> FEATURE:
<221> NAME/KEY: misc_feature
<222> LOCATION: (5)
<223> OTHER INFORMATION: Xaa is leucine (L) or arginine (R)
<220> FEATURE:
<221> NAME/KEY: misc_feature
<222> LOCATION: (6)
<223> OTHER INFORMATION: Xaa is aspartic acid (D), histidine (H), or
      tyrosine (Y) (e.g., D or Y)
<220> FEATURE:
<221> NAME/KEY: misc_feature
<222> LOCATION: (7)
```

```
<223> OTHER INFORMATION: Xaa is serine (S) or proline (P)

<400> SEQUENCE: 25

Xaa Xaa Ser Xaa Xaa Xaa Xaa
  1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic CDR-L3
<220> FEATURE:
<221> NAME/KEY: misc_feature
<222> LOCATION: (3)
<223> OTHER INFORMATION: Xaa is serine (S), glycine (G), aspartic acid
      (D), or tyrosine (Y) (e.g., S or D)
<220> FEATURE:
<221> NAME/KEY: misc_feature
<222> LOCATION: (4)
<223> OTHER INFORMATION: Xaa is asparagine (N), tyrosine (Y), or serine
      (S) (e.g., N or Y)
<220> FEATURE:
<221> NAME/KEY: misc_feature
<222> LOCATION: (5)
<223> OTHER INFORMATION: Xaa is glutamic acid (E), threonine (T), or
      lysine (K) (e.g., E or T)
<220> FEATURE:
<221> NAME/KEY: misc_feature
<222> LOCATION: (6)
<223> OTHER INFORMATION: Xaa is aspartic acid (D), serine (S), or
      leucine (L) (e.g., D or S)
<220> FEATURE:
<221> NAME/KEY: misc_feature
<222> LOCATION: (8)
<223> OTHER INFORMATION: Xaa is leucine (L), tryptophan (W), or tyrosine
      (Y) (e.g., L or W)

<400> SEQUENCE: 26

Gln Gln Xaa Xaa Xaa Xaa Pro Xaa Thr
  1               5

<210> SEQ ID NO 27
<211> LENGTH: 496
<212> TYPE: PRT
<213> ORGANISM: Artificial Sequence
<220> FEATURE:
<223> OTHER INFORMATION: Synthetic human Ang-2 (Accession # O15123)

<400> SEQUENCE: 27

Met Trp Gln Ile Val Phe Phe Thr Leu Ser Cys Asp Leu Val Leu Ala
  1               5                  10                  15

Ala Ala Tyr Asn Asn Phe Arg Lys Ser Met Asp Ser Ile Gly Lys Lys
             20                  25                  30

Gln Tyr Gln Val Gln His Gly Ser Cys Ser Tyr Thr Phe Leu Leu Pro
         35                  40                  45

Glu Met Asp Asn Cys Arg Ser Ser Ser Ser Pro Tyr Val Ser Asn Ala
     50                  55                  60

Val Gln Arg Asp Ala Pro Leu Glu Tyr Asp Asp Ser Val Gln Arg Leu
 65                  70                  75                  80

Gln Val Leu Glu Asn Ile Met Glu Asn Asn Thr Gln Trp Leu Met Lys
                 85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
        115                 120                 125
```

```
Thr Asn Leu Leu Asn Gln Thr Ala Glu Gln Thr Arg Lys Leu Thr Asp
        130                 135                 140
Val Glu Ala Gln Val Leu Asn Gln Thr Thr Arg Leu Glu Leu Gln Leu
145                 150                 155                 160
Leu Glu His Ser Leu Ser Thr Asn Lys Leu Glu Lys Gln Ile Leu Asp
                165                 170                 175
Gln Thr Ser Glu Ile Asn Lys Leu Gln Asp Lys Asn Ser Phe Leu Glu
            180                 185                 190
Lys Lys Val Leu Ala Met Glu Asp Lys His Ile Ile Gln Leu Gln Ser
        195                 200                 205
Ile Lys Glu Glu Lys Asp Gln Leu Gln Val Leu Val Ser Lys Gln Asn
    210                 215                 220
Ser Ile Ile Glu Glu Leu Glu Lys Lys Ile Val Thr Ala Thr Val Asn
225                 230                 235                 240
Asn Ser Val Leu Gln Lys Gln Gln His Asp Leu Met Glu Thr Val Asn
                245                 250                 255
Asn Leu Leu Thr Met Met Ser Thr Ser Asn Ser Ala Lys Asp Pro Thr
            260                 265                 270
Val Ala Lys Glu Glu Gln Ile Ser Phe Arg Asp Cys Ala Glu Val Phe
        275                 280                 285
Lys Ser Gly His Thr Thr Asn Gly Ile Tyr Thr Leu Thr Phe Pro Asn
    290                 295                 300
Ser Thr Glu Glu Ile Lys Ala Tyr Cys Asp Met Glu Ala Gly Gly Gly
305                 310                 315                 320
Gly Trp Thr Ile Ile Gln Arg Arg Glu Asp Gly Ser Val Asp Phe Gln
                325                 330                 335
Arg Thr Trp Lys Glu Tyr Lys Val Gly Phe Gly Asn Pro Ser Gly Glu
            340                 345                 350
Tyr Trp Leu Gly Asn Glu Phe Val Ser Gln Leu Thr Asn Gln Gln Arg
        355                 360                 365
Tyr Val Leu Lys Ile His Leu Lys Asp Trp Glu Gly Asn Glu Ala Tyr
    370                 375                 380
Ser Leu Tyr Glu His Phe Tyr Leu Ser Ser Glu Glu Leu Asn Tyr Arg
385                 390                 395                 400
Ile His Leu Lys Gly Leu Thr Gly Thr Ala Gly Lys Ile Ser Ser Ile
                405                 410                 415
Ser Gln Pro Gly Asn Asp Phe Ser Thr Lys Asp Gly Asp Asn Asp Lys
            420                 425                 430
Cys Ile Cys Lys Cys Ser Gln Met Leu Thr Gly Gly Trp Trp Phe Asp
        435                 440                 445
Ala Cys Gly Pro Ser Asn Leu Asn Gly Met Tyr Tyr Pro Gln Arg Gln
    450                 455                 460
Asn Thr Asn Lys Phe Asn Gly Ile Lys Trp Tyr Tyr Trp Lys Gly Ser
465                 470                 475                 480
Gly Tyr Ser Leu Lys Ala Thr Thr Met Met Ile Arg Pro Ala Asp Phe
                485                 490                 495
```

<210> SEQ ID NO 28
<211> LENGTH: 121
<212> TYPE: PRT
<213> ORGANISM: Artificial Sequence
<220> FEATURE:
<223> OTHER INFORMATION: Synthetic heavy chain variable region
      (e.g., for SAIT-ANG-2-AB-m1A10)

<400> SEQUENCE: 28

-continued

Gln Val Gln Leu Gln Gln Ser Gly Ala Glu Leu Met Lys Pro Gly Ala
1               5                   10                  15

Ser Val Lys Ile Ser Cys Lys Ala Thr Asp Tyr Thr Phe Ser Ser Tyr
            20                  25                  30

Trp Leu Glu Trp Leu Ile Gln Arg Pro Gly His Gly Leu Glu Trp Ile
        35                  40                  45

Gly Glu Ile Leu Pro Gly Ser Gly Ser Thr Asn Tyr Asn Glu Lys Phe
    50                  55                  60

Arg Gly Lys Ala Thr Phe Thr Glu Asp Thr Ser Ser Asn Thr Ala Tyr
65              70                  75                  80

Met Gln Leu Ser Ser Leu Thr Ser Glu Asp Ser Ala Val Tyr Tyr Cys
                85                  90                  95

Ala Arg Gly Asn His Asn Ser Tyr Tyr Tyr Ala Met Asp Tyr Trp Gly
            100                 105                 110

Gln Gly Thr Ser Val Thr Val Ser Ser
        115                 120

<210> SEQ ID NO 29
<211> LENGTH: 120
<212> TYPE: PRT
<213> ORGANISM: Artificial Sequence
<220> FEATURE:
<223> OTHER INFORMATION: Synthetic heavy chain variable region
      (e.g., for SAIT-ANG-2-AB-m8D3)

<400> SEQUENCE: 29

Glu Val Gln Leu Gln Gln Ser Gly Pro Glu Leu Val Lys Pro Gly Asp
1               5                   10                  15

Ser Val Lys Met Ser Cys Lys Ala Ser Gly Tyr Thr Phe Thr Asp Tyr
            20                  25                  30

Tyr Met Lys Trp Val Arg Gln Ser His Gly Lys Ser Leu Gln Trp Val
        35                  40                  45

Gly Glu Ile Asn Pro Lys Asn Gly Asp Thr Phe Tyr Asn Gln Ile Phe
    50                  55                  60

Lys Gly Lys Ala Thr Leu Thr Val Asp Lys Ser Ser Ser Thr Ala Tyr
65              70                  75                  80

Met Gln Leu Thr Ser Leu Thr Ser Glu Asp Ser Ala Val Tyr Tyr Cys
                85                  90                  95

Thr Arg Glu Asn Asp Tyr Asp Val Gly Phe Phe Asp Tyr Trp Gly Gln
            100                 105                 110

Gly Thr Ser Val Thr Val Ser Ser
        115                 120

<210> SEQ ID NO 30
<211> LENGTH: 118
<212> TYPE: PRT
<213> ORGANISM: Artificial Sequence
<220> FEATURE:
<223> OTHER INFORMATION: Synthetic heavy chain variable region
      (e.g., for SAIT-ANG-2-AB-m1B6)

<400> SEQUENCE: 30

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
            50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                85                  90                  95

Ala Arg Asp His Asp Gly Tyr Leu Met Asp Tyr Trp Gly Gln Gly Thr
                100                 105                 110

Ser Val Thr Val Ser Ser
        115

<210> SEQ ID NO 31
<211> LENGTH: 118
<212> TYPE: PRT
<213> ORGANISM: Artificial Sequence
<220> FEATURE:
<223> OTHER INFORMATION: Synthetic heavy chain variable region
      (e.g., for SAIT-ANG-2-AB-m3E2)

<400> SEQUENCE: 31

Glu Val Gln Leu Gln Gln Ser Gly Ala Glu Leu Val Lys Pro Gly Ala
 1               5                   10                  15

Ser Val Lys Leu Ser Cys Thr Ala Ser Gly Phe Asn Ile Lys Asp Pro
                20                  25                  30

Tyr Ile His Trp Val Lys Gln Arg Pro Glu Gln Gly Leu Glu Trp Ile
            35                  40                  45

Gly Arg Ile Asp Pro Ala Asn Gly Asn Thr Lys Tyr Asp Pro Lys Phe
        50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                85                  90                  95

Val Arg Arg Trp Asp Gly Gly Phe Asp Tyr Trp Gly Gln Gly Thr
                100                 105                 110

Ser Val Thr Val Ser Ser
        115

<210> SEQ ID NO 32
<211> LENGTH: 363
<212> TYPE: DNA
<213> ORGANISM: Artificial Sequence
<220> FEATURE:
<223> OTHER INFORMATION: Synthetic gene encoding heavy chain variable
      region (e.g., for SAIT-ANG-2-AB-m1A10)

<400> SEQUENCE: 32
caggttcagc tgcagcagtc tggagctgag ctgatgaagc ctggggcctc agtgaagata      60
tcctgcaagg ctactgacta cacattcagt agctactggc tagagtggtt aatacagagg     120
cctggacatg gccttgagtg gattggagag attttacctg gaagtggtag tactaactac     180
aatgagaagt tcaggggcaa ggccacattc actgaagata tcctccaa cacagcctac       240 atgcaactca gcagcctgac atctgaggac tctgccgtct attactgtgc aagaggtaac     300
cacaactcct attactatgc tatggactac tggggtcaag gaacctcagt caccgtctcc     360
tca                                                                    363

<210> SEQ ID NO 33
<211> LENGTH: 360

<212> TYPE: DNA
<213> ORGANISM: Artificial Sequence
<220> FEATURE:
<223> OTHER INFORMATION: Synthetic gene encoding heavy chain variable region (e.g., for SAIT-ANG-2-AB-m8D3)

<400> SEQUENCE: 33

```
gaggtccagc tgcaacagtc tggacctgag ctggtgaagc ctggggattc agtgaagatg    60
tcctgcaagg cttctggata caccttcact gactactaca tgaagtgggt gaggcagagc   120
catggaaaga gccttcagtg ggttggagaa attaatccta agaatggtga tactttctac   180
aaccagatat tcaagggcaa ggccacattg actgtagaca atcctccag cacagcctac    240
atgcaactca ccagcctgac atctgaggac tctgcagtct attactgtac acgtgagaat   300
gattacgacg tgggattctt tgactactgg ggtcaaggaa cctcagtcac cgtctcctca   360
```

<210> SEQ ID NO 34
<211> LENGTH: 354
<212> TYPE: DNA
<213> ORGANISM: Artificial Sequence
<220> FEATURE:
<223> OTHER INFORMATION: Synthetic gene encoding heavy chain variable region (e.g., for SAIT-ANG-2-AB-m1B6)

<400> SEQUENCE: 34

```
cagatccagt tggtgcagtc tggacctgag ctgaagaagc ctggagagac agtcaagatc    60
tcctgcaagg cttctggata taccttcaca aactatggaa tgaactgggt gaagcaggct   120
ccaggaaagg gtttaaagtg gatgggctgg ataaacacct acactggaga gccaacatat   180
gctgatgact caagggacg ttttgccttc tctttggaaa cctctgccag cactgcctat    240
ttgcagatca caacctcaa aaatgaggac acggctacat atttctgtgc aagagatcat    300
gatggttacc ttatggacta ctggggtcaa ggaacctcag tcaccgtctc ctca          354
```

<210> SEQ ID NO 35
<211> LENGTH: 354
<212> TYPE: DNA
<213> ORGANISM: Artificial Sequence
<220> FEATURE:
<223> OTHER INFORMATION: Synthetic gene encoding heavy chain variable region (e.g., for SAIT-ANG-2-AB-m3E2)

<400> SEQUENCE: 35

```
gaggttcagc tgcagcagtc tggggcagag cttgtgaagc caggggcctc agtcaagttg    60
tcctgcacag cttctggctt caacattaaa gaccccctata tacactgggt gaaacagagg  120
cctgaacagg gcctggagtg gattggaagg attgatcctg cgaatggtaa tactaaatat   180
gacccgaagt tccagggcaa ggccactata acggcagaca catcctccaa cacagcctac   240
ctccagctca gcagcctgac atctgaggac actgccgtct attactgtgt tagaaggtgg   300
gacggggggg gctttgacta ctggggtcaa ggaacctcag tcaccgtctc ctca          354
```

<210> SEQ ID NO 36
<211> LENGTH: 111
<212> TYPE: PRT
<213> ORGANISM: Artificial Sequence
<220> FEATURE:
<223> OTHER INFORMATION: Synthetic light chain variable region (e.g., for SAIT-ANG-2-AB-m1A10)

<400> SEQUENCE: 36

Asp Ile Val Leu Thr Gln Ser Pro Ala Ser Leu Ala Val Ser Leu Gly
 1               5                  10                  15

```
Gln Arg Ala Thr Ile Ser Cys Arg Ala Ser Glu Ser Val Asp Ser Tyr
                20                  25                  30

Gly Asn Ser Phe Met His Trp Tyr Gln Gln Lys Pro Gly Gln Pro Pro
            35                  40                  45

Lys Leu Leu Ile Tyr Arg Ala Ser Asn Leu Asp Ser Gly Ile Pro Ala
 50                  55                  60

Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Ser Asn
                85                  90                  95

Glu Asp Pro Leu Thr Phe Gly Ala Gly Thr Lys Leu Glu Leu Lys
            100                 105                 110

<210> SEQ ID NO 37
<211> LENGTH: 107
<212> TYPE: PRT
<213> ORGANISM: Artificial Sequence
<220> FEATURE:
<223> OTHER INFORMATION: Synthetic light chain variable region (e.g.,
      for SAIT-ANG-2-AB-m8D3)

<400> SEQUENCE: 37

Thr Ile Val Met Thr Gln Thr Pro Lys Phe Leu Leu Val Ser Ala Gly
 1               5                  10                  15

Asp Arg Ile Thr Ile Thr Cys Lys Ala Ser Gln Ser Val Ser Asn Asp
                20                  25                  30

Val Ala Trp Tyr Gln Gln Lys Pro Gly Gln Ser Pro Lys Leu Leu Ile
            35                  40                  45

Tyr Tyr Ala Ser Asn Arg Tyr Pro Gly Val Pro Asp Arg Phe Thr Gly
 50                  55                  60

Ser Gly Tyr Gly Thr Asp Phe Thr Phe Thr Ile Ser Thr Val Gln Ala
 65                  70                  75                  80

Glu Asp Leu Ala Val Tyr Phe Cys Gln Gln Asp Tyr Thr Ser Pro Trp
                85                  90                  95

Thr Phe Gly Gly Gly Thr Glu Leu Glu Ile Lys
            100                 105

<210> SEQ ID NO 38
<211> LENGTH: 107
<212> TYPE: PRT
<213> ORGANISM: Artificial Sequence
<220> FEATURE:
<223> OTHER INFORMATION: Synthetic light chain variable region (e.g.,
      for SAIT-ANG-2-AB-m1B6)

<400> SEQUENCE: 38

Asp Ile Gln Met Thr Gln Thr Thr Ser Ser Leu Ser Ala Ser Leu Gly
 1               5                  10                  15

Asp Arg Val Thr Ile Ser Cys Ser Thr Ser Gln Gly Ile Ser Asn Tyr
                20                  25                  30

Leu Asn Trp Tyr Gln Gln Lys Pro Asp Gly Thr Val Lys Leu Leu Ile
            35                  40                  45

Phe Tyr Thr Ser Ser Leu His Ser Gly Val Pro Ser Arg Phe Ser Gly
 50                  55                  60

Ser Gly Ser Gly Thr Asp Tyr Ser Leu Thr Ile Ser Asn Leu Glu Pro
 65                  70                  75                  80

Glu Asp Ile Ala Thr Tyr Tyr Cys Gln Gln Tyr Ser Lys Leu Pro Tyr
                85                  90                  95
```

```
Thr Phe Gly Gly Gly Thr Lys Leu Glu Ile Lys
            100                 105
```

<210> SEQ ID NO 39
<211> LENGTH: 107
<212> TYPE: PRT
<213> ORGANISM: Artificial Sequence
<220> FEATURE:
<223> OTHER INFORMATION: Synthetic light chain variable region (e.g.,
      for SAIT-ANG-2-AB-m3E2)

<400> SEQUENCE: 39

```
Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Thr Asn Leu Glu Gln
 65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105
```

<210> SEQ ID NO 40
<211> LENGTH: 333
<212> TYPE: DNA
<213> ORGANISM: Artificial Sequence
<220> FEATURE:
<223> OTHER INFORMATION: Synthetic gene encoding light chain variable
      region (e.g., for SAIT-ANG-2-AB-m1A10)

<400> SEQUENCE: 40

```
gacattgtgc tgacccaatc tccagcttct ctggctgtgt ctctaggtca gagggccacc    60
atatcctgca gagccagtga aagtgttgat agttatggca atagttttat gcactggtac   120
cagcagaaac aggacagcc acccaaactc ctcatctatc gtgcatccaa cctagattct   180
gggatccctg ccaggttcag tggcagtggg tctaggacag acttcaccct caccattaat   240
cctgtggagg ctgatgatgt tgcaacctat tactgtcagc aaagtaatga ggatcctctc   300
acgttcggtg ctgggaccaa gctggagctg aaa                                333
```

<210> SEQ ID NO 41
<211> LENGTH: 321
<212> TYPE: DNA
<213> ORGANISM: Artificial Sequence
<220> FEATURE:
<223> OTHER INFORMATION: Synthetic gene encoding light chain variable
      region (e.g., for SAIT-ANG-2-AB-m8D3)

<400> SEQUENCE: 41

```
actattgtga tgacccagac tcccaaattc ctgcttgtat cagcaggaga caggattacc    60
ataacctgca aggccagtca gagtgtgagt aatgatgtag cctggtatca acagaagcca   120
gggcagtctc ctaaactgct gatatactat gcatccaatc gctacctgg agtccctgat   180 cgcttcactg gcagtggata tgggacggat ttcactttca ccatcagcac tgtgcaggct   240
gaagacctgg cagtttattt ctgtcagcag gattataccc tccgtggac gttcggtgga   300
```

-continued

```
ggcaccgagc tggaaatcaa a                                        321

<210> SEQ ID NO 42
<211> LENGTH: 321
<212> TYPE: DNA
<213> ORGANISM: Artificial Sequence
<220> FEATURE:
<223> OTHER INFORMATION: Synthetic gene encoding light chain variable
      region (e.g., for SAIT-ANG-2-AB-m1B6)

<400> SEQUENCE: 42
gatatccaga tgacacagac tacatcctcc ctgtctgcct ctctgggaga cagagtcacc    60
atcagttgta gtacaagtca gggcattagc aattatttga actggtatca gcagaaacca   120
gatggaactg ttaaactcct gatcttttac acatcaagtt tacactcagg agtcccatca   180
aggttcagtg gcagtgggtc tgggactgat tattctctca ccatcagcaa cctggaacct   240
gaagatattg ccacttacta ttgtcagcag tatagtaagc ttccgtacac gttcggggg    300 gggaccaagc tggaaataaa a                                             321

<210> SEQ ID NO 43
<211> LENGTH: 321
<212> TYPE: DNA
<213> ORGANISM: Artificial Sequence
<220> FEATURE:
<223> OTHER INFORMATION: Synthetic gene encoding light chain variable
      region (e.g., for SAIT-ANG-2-AB-m3E2)

<400> SEQUENCE: 43
gatatccaga tgacacagac tacatcctcc ctgtctgcct ctctgggaga cagagtcacc    60
atcagttgca gggcaagtca ggacattagc aattatttaa actggtatca gcagaaacca   120
gatggaactg ttaaactcct gatctactac acatcaagat tacactcagg agtcccatca   180
aggttcagtg gcagtgggtc tggaacagat tattctctca ccattaccaa cctggagcaa   240
gaagatattg ccacttactt ttgccaacag ggtaatacgc ttccgtggac gttcggtgga   300
ggcaccaagc tggaaatcaa a                                             321
```